(12) United States Patent
Beyette, Jr. et al.

(10) Patent No.: US 8,027,814 B2
(45) Date of Patent: Sep. 27, 2011

(54) METHODS FOR ASSESSING A CONDITION BY ANALYZING BLOOD IN CEREBROSPINAL FLUID

(75) Inventors: Fred R. Beyette, Jr., Cincinnati, OH (US); Joseph F. Clark, Cincinnati, OH (US); Chad J. Morgan, Springfield, MO (US); James J. Caffery, Jr., Cincinnati, OH (US); Prashant Bhadri, Pica Rivera, CA (US); Gail Pyne-Geithman, Cincinnati, OH (US); Anindya Majumder, San Diego, CA (US)

(73) Assignee: University of Cincinnati, Cincinnati, OH (US)

( * ) Notice: Subject to any disclaimer, the term of this patent is extended or adjusted under 35 U.S.C. 154(b) by 854 days.

(21) Appl. No.: 11/194,878

(22) Filed: Aug. 1, 2005
(Under 37 CFR 1.47)

(65) Prior Publication Data
US 2006/0034730 A1    Feb. 16, 2006

Related U.S. Application Data

(60) Provisional application No. 60/592,502, filed on Jul. 30, 2004.

(51) Int. Cl.
*G06F 17/10* (2006.01)
(52) U.S. Cl. .................. 703/2; 702/19; 702/23; 703/11; 356/319
(58) Field of Classification Search .................. None
See application file for complete search history.

(56) References Cited

U.S. PATENT DOCUMENTS 6,720,193 B2 * 4/2004 Hage et al. .................... 436/518

OTHER PUBLICATIONS

Strand, "Evaluation of long-term outcome and safety after hemodilution therapy in acute ischemic stroke", 1992, Stroke, vol. 23, pp. 657-662.*
van Dijk et al., "Diagnosis of Perimesencephalic Nonaneurysmal Subarachnoid Hemorrhage With Computed Tomography", 2001, Journal of Stroke and Cerebrovascular Diseases, vol. 10, No. 6, pp. 247-251.*
Cruickshank, "CSF spectrophotometry in the diagnosis of subarachnoid haemorrhage", 2001, Journal of Clinical Pathology, vol. 54, pp. 827-830.*

* cited by examiner

*Primary Examiner* — Carolyn L. Smith
(74) *Attorney, Agent, or Firm* — Dinsmore & Shohl LLP

(57) ABSTRACT

The present invention provides methods for assessing a condition in an individual by analyzing a cerebrospinal fluid sample from the individual, for example, by spectroscopy. Further, the invention provides methods for determining an amount of blood in the cerebrospinal fluid sample; methods for determining concentrations of analytes in the cerebrospinal fluid sample; methods for determining a length of time the blood has been in the cerebrospinal fluid sample; and methods for rapidly obtaining a differential diagnosis between conditions indicated by blood in the cerebral spinal fluid. Moreover, the present invention provides instruments capable of rapidly assessing a condition in and individual by point-of-care analysis of a cerebral fluid sample from an individual.

26 Claims, 19 Drawing Sheets

| α11 β11 | α12 β12 | α13 β13 | α14 β14 | α15 β15 |
|---------|---------|---------|---------|---------|
| α21 β21 | α22 β22 | α23 β23 | α24 β24 | α25 β25 |
| α31 β31 | α32 β32 | α33 β33 | α34 β34 | α35 β35 |
| α41 β41 | α42 β42 | α43 β43 | α44 β44 | α45 β45 |
| α51 β51 | α52 β52 | α53 β53 | α54 β54 | α55 β55 |

Increasing Concentration of M(n) (vertical axis)
Increasing Concentration of B(n) (horizontal axis)

Fig. 13

METHODS FOR ASSESSING A CONDITION BY ANALYZING BLOOD IN CEREBROSPINAL FLUID

RELATED APPLICATIONS

This application claims priority under 35 U.S.C. §119 of U.S. Provisional Application Ser. No. 60/592,502, filed Jul. 30, 2004.

GOVERNMENT INTERESTS

This invention was made, at least in part, with funds from the Federal Government, awarded through grants numbered R01 HL67186, R01 NS042308, and R21 NS4697. The U.S. Government therefore has certain acknowledged rights to the invention.

FIELD OF THE INVENTION

The present invention is directed toward methods for assessing a condition in an individual by analyzing a cerebrospinal fluid sample from an individual, for example, by spectroscopy. Further, the invention is directed towards methods for determining an amount of blood in the cerebrospinal fluid sample; methods for determining concentrations of analytes in the cerebrospinal fluid sample; and methods for determining a length of time the blood has been in the cerebrospinal fluid sample. Moreover, the present invention provides an instrument capable of rapidly assessing a condition in and individual by point-of-care analysis of a cerebral fluid sample from an individual.

BACKGROUND OF THE INVENTION

A cerebral aneurysm is a weakened and diseased portion of an artery in the brain. When a cerebral aneurysm ruptures, the brain is bathed in blood, and a specific type of bleeding known as a subarachnoid hemorrhage (SAH) occurs. Approximately fifty percent of patients die immediately after an aneurysm ruptures, and no test exists currently to screen people for the presence of a cerebral aneurysm. The diagnosis of a SAH is made only after an aneurysm ruptures, and the literature indicates that 23-51% of patients with a SAH are originally misdiagnosed with the average delay in diagnosis being 6 days. At present, clinicians do not possess the diagnostic modalities sufficient for assessing patients with a suspected ruptured cerebral aneurysm and a normal computerized tomography (CT) scan.

In patients with a suspected SAH and a negative CT scan, the performance of a lumbar puncture (LP) is strongly recommended. Typically, a needle is used to sample the fluid surrounding the spinal cord in LP. Collected from the patient's lumbar spine, the cerebrospinal fluid communicates with the fluid around the brain and is tainted with blood after an aneurysm ruptures. In other words, the presence of blood in the CSF raises the possibility of a SAH. The difficulty with the performance of a spinal tap is that nearly 1 in 5 of these procedures results in a "traumatic tap". This term implies the needle used for collection of the CSF penetrated a blood vessel in the patient's back prior to entering the space where the CSF is found. In these circumstances, part of the sample is the patient's CSF and a portion is from a blood vessel in the muscle, bone or a ligament of the spine. At present, no test can reliably identify the source of blood in CSF and differentiate a SAH from a traumatic spinal tap. A correct diagnosis is critical to directing patients toward repair of their cerebral aneurysm before another rupture occurs.

About 2 million people in the United States are thought to harbor a cerebral aneurysm, while an SAH affects 30,000 people per year. To detect a small or sentinel SAH, CSF analysis should be rapid and sensitive. Likewise, the specificity of CSF analysis is crucial, and the misinterpretation of a traumatic spinal tap as a SAH may lead to the treatment of an un-ruptured aneurysm. If the CSF contains zero or very few red blood cells, a diagnosis of SAH is extremely unlikely. The difficulty arises when large numbers of (red blood cells) RBC's are found. At present, no method of CSF analysis has the ability to fully direct a patient's care.

A key concept to the differentiation of a SAH from a traumatic tap is the identification of a marker for SAH. The measurement of CSF bilirubin, if collected 12 hours after the onset of symptoms, can distinguish between a SAH and a traumatic spinal tap. Furthermore, the production of bilirubin occurs over a predictable time-course and can be detected following a low volume SAH. Effectively, the presence of elevated CSF bilirubin excludes the diagnosis of a traumatic tap. Hence, methods are needed for rapidly assessing a condition of elevated CSF bilirubin in an individual suspected of having suffered from an SAH.

The determination of blood in the CSF is frequently done simply with a visual inspection for xanthochromia, a discoloration of the CSF indicating the presence of blood. This subjective and low sensitivity technique cannot determine the amount of blood in the CSF or the degradative processes that have acted on the blood. Nor can this visual inspection estimate the amount of time the blood has been in the CSF. The results of visual interpretation of spectra are qualitative in nature and depend strongly on the experience of the technicians; results, therefore, are prone to large inter- and intra-individual variation. Thus, there exists a substantial need for improved methods for analyzing blood in the CSF to assess a condition, such as a hemorrhage and methods are needed which objectively quantify spectral output and do not depend on the skills of the technician.

Similar needs existed and were developed in the field of diabetic study to quantify glucose in blood. In measurements of blood glucose, the doctors withdraw some quantity of blood and analyze it. To extract the glucose information in the presence of other constituents, spectral analysis is performed where different physiological components produce spectral signals. The main idea is to separate the glucose signals from the other dominating signals in the spectra. There have been a number of ways to find a solution for this problem using mathematical algorithms. These include, for example, the methods of principal components regression (PCR), partial least squares (PLS), and artificial neural networks (ANN).

Performance reliability and validity of the signal processing is very dependent on the quality of the data. The PLS and the ANN algorithmic models are not always dependable because they are sensitive to the changes in time and the resultant variance in data that varies with the concentration of the solution. Moreover, given their complexity they are more appropriate to implement when multiple variables need to be predicted. Other work has concentrated on using pattern recognition algorithms to extract the respective signals. It has been reported that derivative analysis of the absorption or transmittance spectra can be a useful tool in drastically improving the selectivity of a bilirubin in a mixed component sample. Others have tried to use an extension to the above model by characterizing the absorbance/transmittance curves by Gaussian peaks and then applying the first derivative algorithm. The problem with this work is that the results have been obtained in very diluted samples that are not physiologically achievable and hence have no application to assessment of a condition in an individual by subjecting fluid samples drawn from the individual to those analyses. Recent research has concentrated on the first and the second order derivative applications on the spectral signals of bilirubin and other components to analyze patterns that reflect changes that can be used in analysis. Also, other mathematical algorithms like logarithmic ratios of signals are compared to extract the wanted component. None of the above work has been applied to describe aneurysm models or SAH models.

SUMMARY OF THE INVENTION

Accordingly, it is an object of the present invention to provide physicians with a tool to accurately diagnose patients with a suspected SAH and to provide point-of-care technology that will allow completion of the diagnostic paradigm using a point-of-care measurement of bilirubin. The present invention also provides a standardized method for the spectrophotometric examination of CSF which yields reliable quantitative results. The detection of a SAH can be accomplished using the characteristic spectral absorption patterns for blood's breakdown products, with the blood product of interest referred to herein as an analyte.

Accordingly, the present invention provides methods for assessing conditions in an individual comprising the steps of: obtaining a cerebrospinal fluid sample from an individual; and analyzing the blood in the cerebrospinal fluid sample. Specific embodiments are directed to methods wherein the blood is analyzed by a spectrophotometer which generates an output signal which may be represented in the form of a spectral absorption curve over certain significant wavelength ranges. Very specific embodiments are directed to methods comprising very specific wavelength ranges.

A further embodiment provides methods for estimating a concentration of an analyte in a fluid comprised of the analyte and a contaminant. Optionally, EDTA may be added to the fluid. The method comprises: (a) using a spectrophotometer to generate at least one standard spectral absorption curve for the analyte and (b) for the contaminant; (c) computing a sum spectral absorption curve for the fluid by adding the spectral absorptions curves for the analyte and contaminant; (d) comparing the spectral absorption curves of the analyte and contaminant to determine wavelength ranges wherein the analyte dominates and wherein the contaminant dominates; (e) obtaining a sample of the fluid and generating a measured spectral absorption curve of the sample over each of those wavelength ranges; (f) computing a scaling factor for both the wavelength range where the analyte dominates for the wavelength range where the contaminant dominates and applying the scaling factors to generate a scaled spectral absorption curve of the fluid; (g) optionally, generating at least one interpolative curve from the standard spectral absorption curves of the analyte and contaminant; (h) using a modified minimum distance algorithm to select which standard contaminant spectral absorption curve of the contaminant is closest in distance to the scaled spectral curve over the wavelength range where the contaminant dominates; (i) computing a residual curve from this over all measured wavelengths; (j) using a modified minimum distance algorithm to select which standard analyte spectral absorption curve is closest in distance to the residual curve over the wavelength range where the analyte dominates; (k) computing a new residual curve from this over all measured wavelengths; and (l) iteratively repeating these steps until a standard contaminant curve and a standard analyte curve are selected in consecutive iterations.

A further embodiment is directed to methods for estimating a concentration of an analyte in a fluid comprised of the analyte and a contaminant, where the method comprises: (a) using a spectrophotometer to generate a standard spectral absorption curve at each of at least two known concentrations of the analyte and at each of at least two known concentrations of the contaminant; (b) computing a first derivative curve of those standard spectral absorption curves; (c) inspecting the first derivative curve of the contaminant to determine a significant wavelength range wherein an average value of the first derivative curve over that range approximates zero; (d) using a spectrophotometer to generate a standard spectral absorption curve for each of at least two samples of the fluid over the significant wavelength range, wherein each sample of the fluid comprises a different known concentration of the analyte and a known fixed concentration of the contaminant; (e) generating a first derivative curve for each of the standard spectral absorption curves so generated, and computing an average value of the first derivative for each of the at least two samples of the fluid over the significant wavelength range; (f) generating a curve by plotting the different known concentrations of the analyte versus the average values of the first derivatives over the significant wavelength range; (g) fitting a polynomial equation to the resulting curve; (h) obtaining a sample of the fluid, generating a spectral absorption curve over the significant wavelength range, computing a value for the average first derivative over the significant wavelength range, plugging the value into the polynomial equation, wherein the resulting value is the estimated concentration of the analyte in the sample of the fluid.

In another embodiment of methods directed to estimating a concentration of an analyte in a fluid comprised of the analyte and a contaminant, and, optionally, EDTA, the method comprises: (a) formulating at least two mock CSF compositions wherein each mock CSF composition has a different known concentration of the analyte and the contaminant; (b) generating a spectral absorption curve for each mock CSF composition; (c) generating an average mock CSF absorption spectral curve, wherein the curve has a shape; (d) determining a first wavelength range wherein both the analyte and the contaminant contribute significantly to the shape of the absorption curve; (e) determining a second wavelength range wherein contribution to the shape of the absorption curve by the analyte is minimal. (f) plotting concentrations of the contaminant versus mean of absorbance across the second wavelength range and using linear regression to generate a contaminant regression model; (g) generating an analyte regression model over the first wavelength; collecting a sample of CSF having unknown concentrations of analyte and contaminant; (h) generating a spectral absorption curve for the sample of CSF; (i) determining an estimated concentration of the contaminant using the contaminant regression model; and (j) entering the estimated concentration of the contaminant into the analyte regression model to generate an estimated concentration of the analyte.

The invention also provides an embodiment directed to an instrument for rapidly assessing a condition of an individual by estimating a concentration of an analyte in a body fluid of the individual. The instrument comprises: a device for analyzing a body fluid of the individual, wherein the device receives a sample of the body fluid and generates an output signal; and a processor which subjects the output signal to an algorithm which yields an estimated value of the concentration of the analyte.

The present invention is advantageous for objectively assessing a condition based upon analyzing the blood in the cerebrospinal fluid sample. Additional embodiments, objects and advantages of the invention will become more fully apparent in view of the following figures and detailed description.

BRIEF DESCRIPTION OF THE DRAWINGS

FIG. 3a: The second derivative of the absorption spectrum shown in FIG. 2a;

FIG. 13: Bilirubin/Methemoglobin (B/M) concentration plane with different scale factors over different regions.

DETAILED DESCRIPTION

Figure 1:
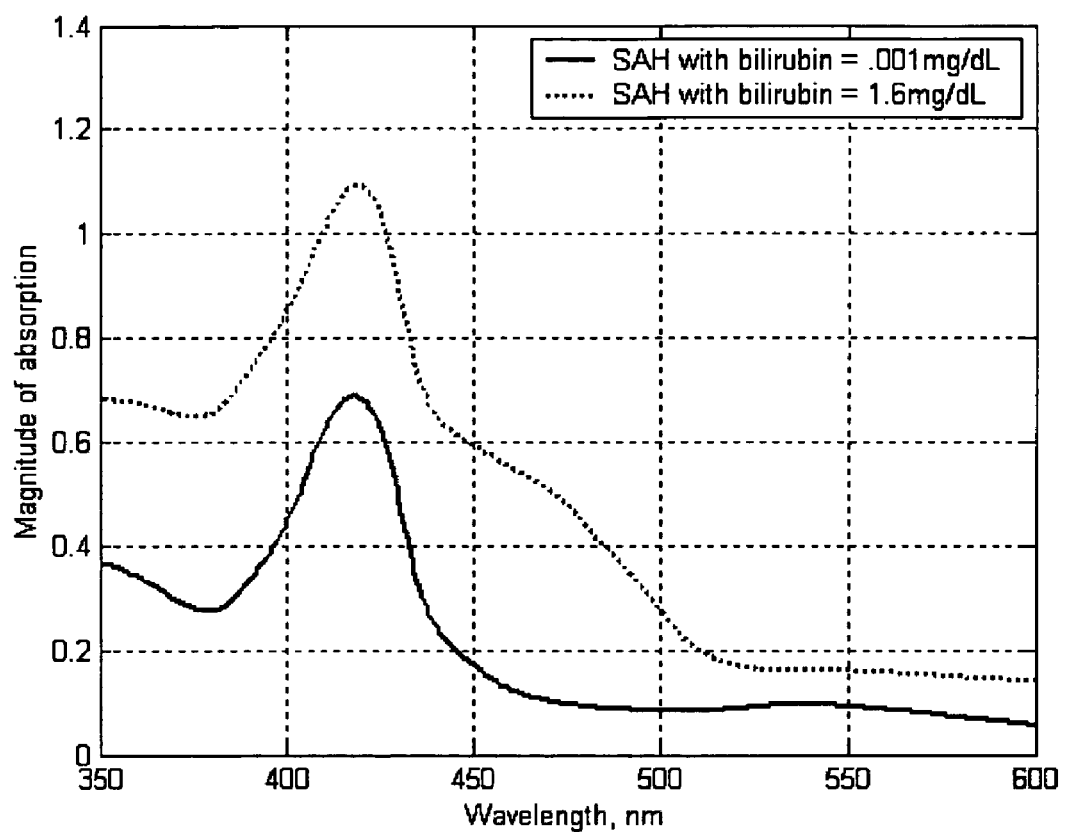
FIG. 1: Spectrophotometer results of CSF following SAH obtained from LP.
Figure 2A:
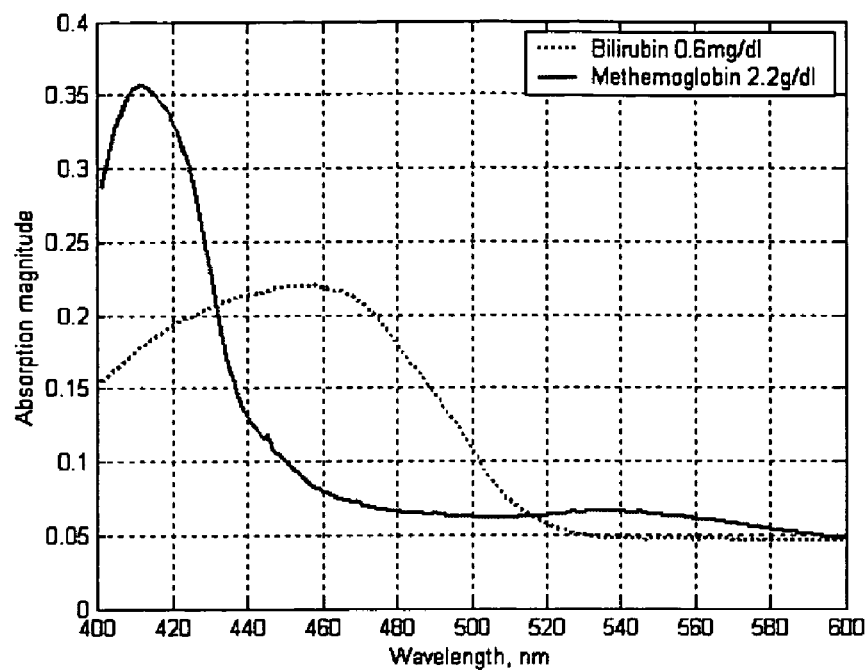
FIG. 2a: Independent absorption spectra of bilirubin (0.6 mg/dl) and methemoglobin (2.2 g/dl)
Figure 2B:
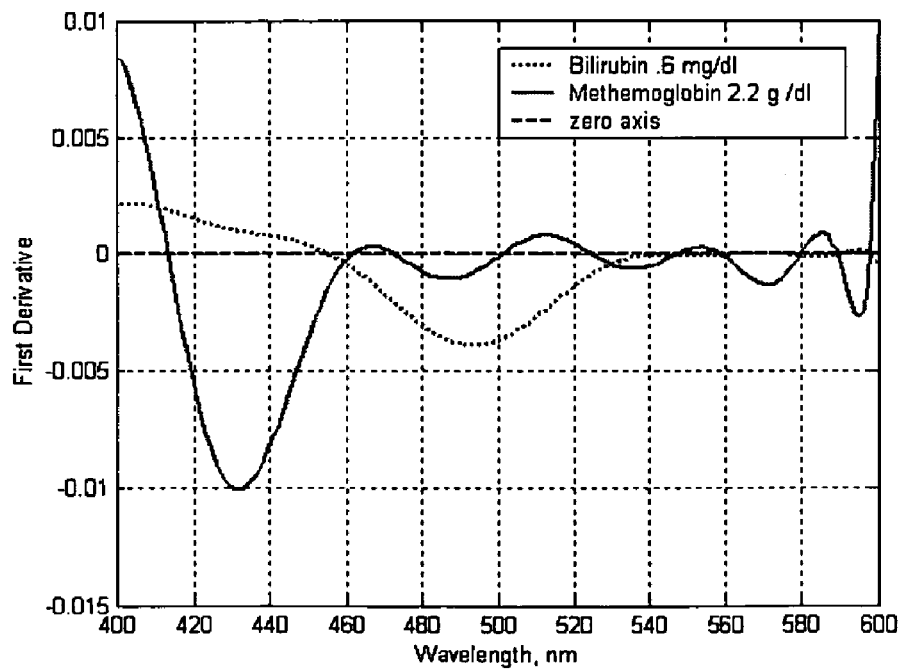
FIG. 2b: The first derivative computed from the absorption spectra in (a)
Figure 3A:
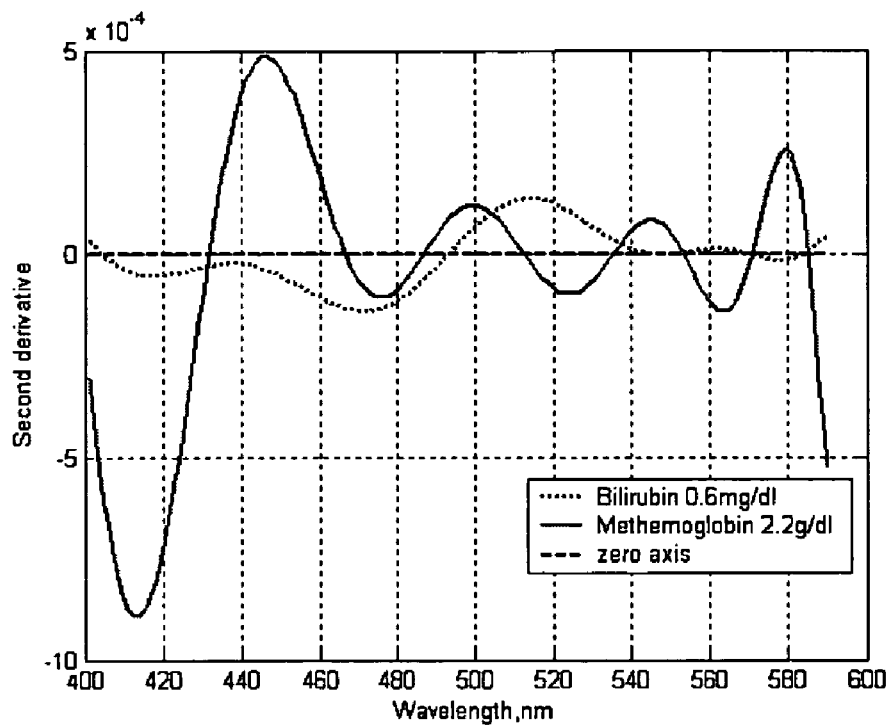
Figure 3B:
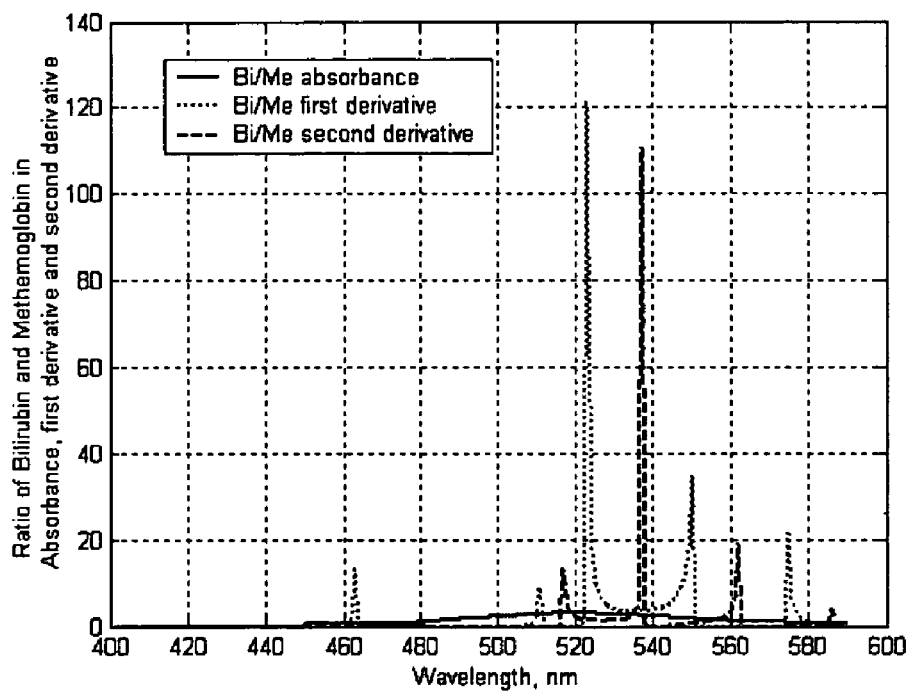
FIG. 3b: The signal to noise ratio (bilirubin/methemoglobin) of their independent absorption spectra, of the first derivative of the absorbance spectra and the second derivative of the absorbance spectra.
Figure 4A:
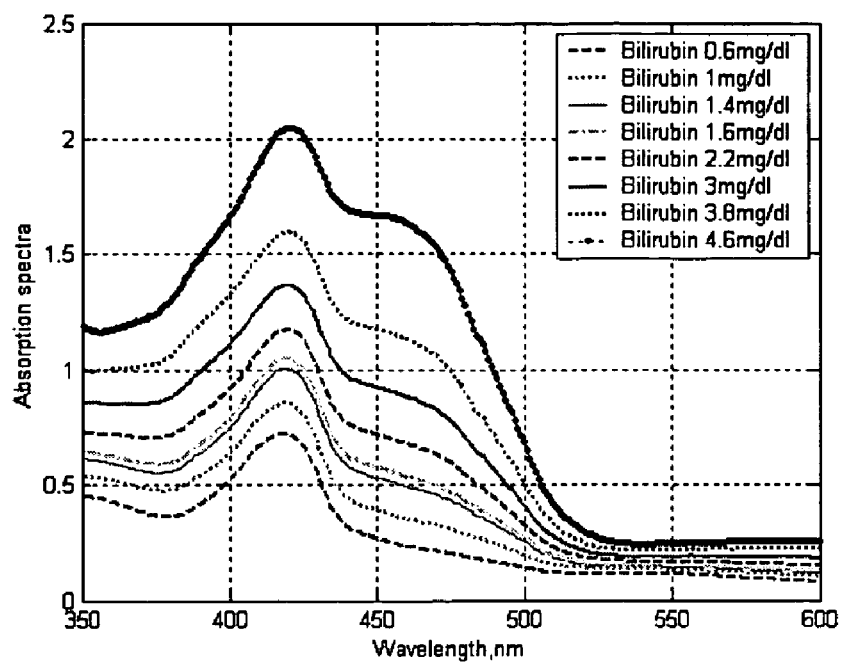
FIG. 4a: The absorption spectrum of solutions containing of varying amounts of bilirubin and a fixed amount of methemoglobin (4.6 g/dl)
Figure 4B:
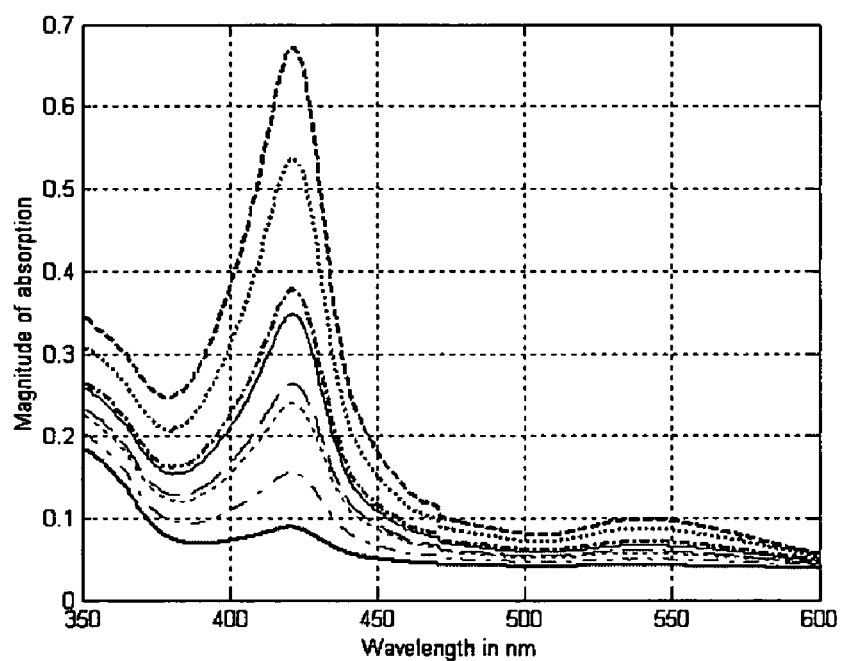
FIG. 4b: The absorption spectrum of solutions containing a fixed amount of bilirubin and varying amounts of methemoglobin. Absorption increases with increasing concentration of methemoglobin.
Figure 5A:
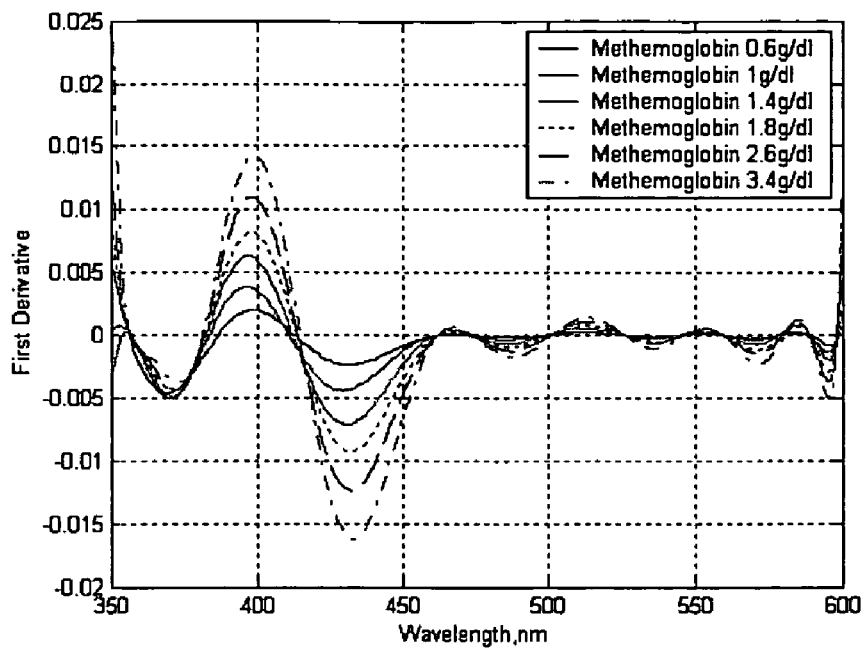
FIG. 5a: The first derivative of the hemoglobin data at different concentrations of hemoglobin. The general trend of the curve remains same at all concentrations.
Figure 5B:
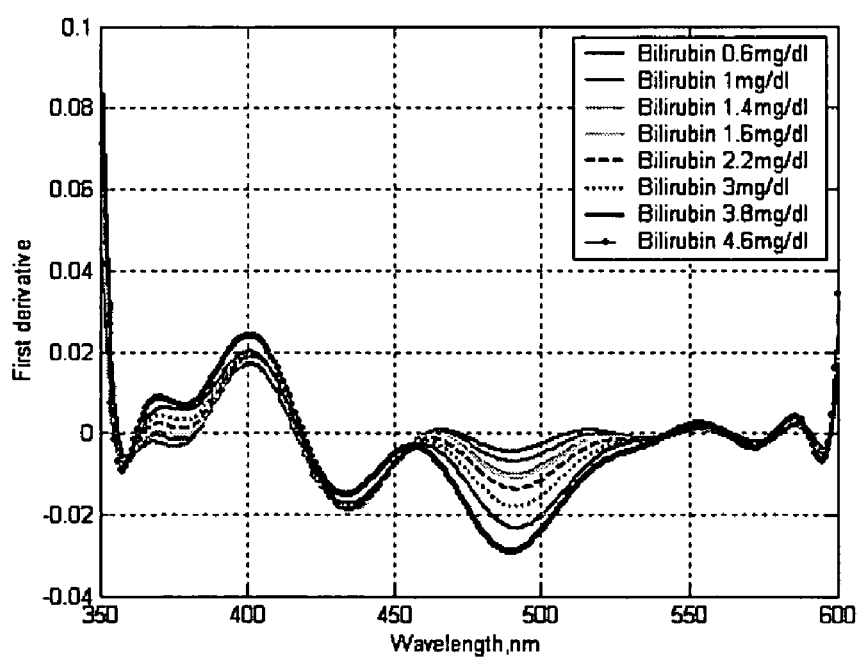
FIG. 5b: The derivative of the data shown in FIG. 5(a). Contains varying amounts of bilirubin and fixed amount of methemoglobin.
Figure 6:
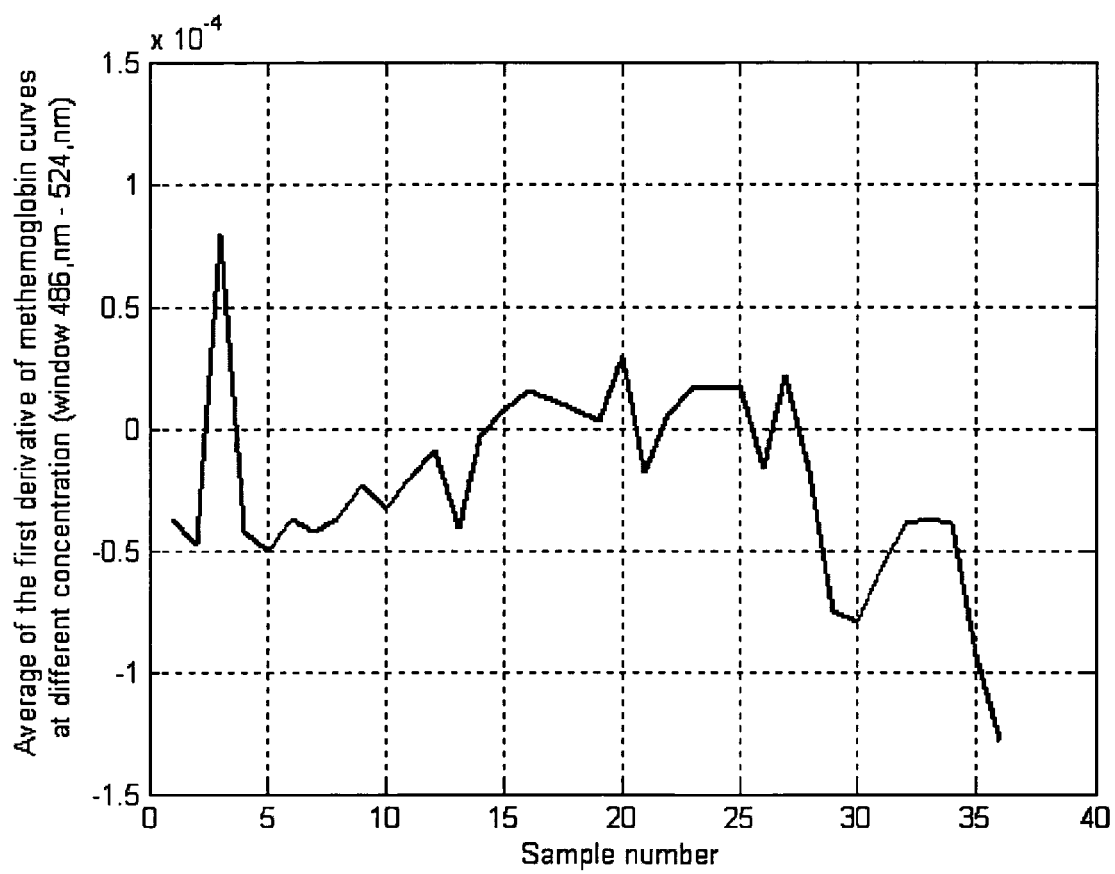
FIG. 6: The first derivative curves of hemoglobin at different concentrations averaged over the window of 486 nm to 524 nm. Each point for a particular sample number indicates the sum of the contributions of first derivative values over the window at that concentration divided by the window size.
Figure 7:
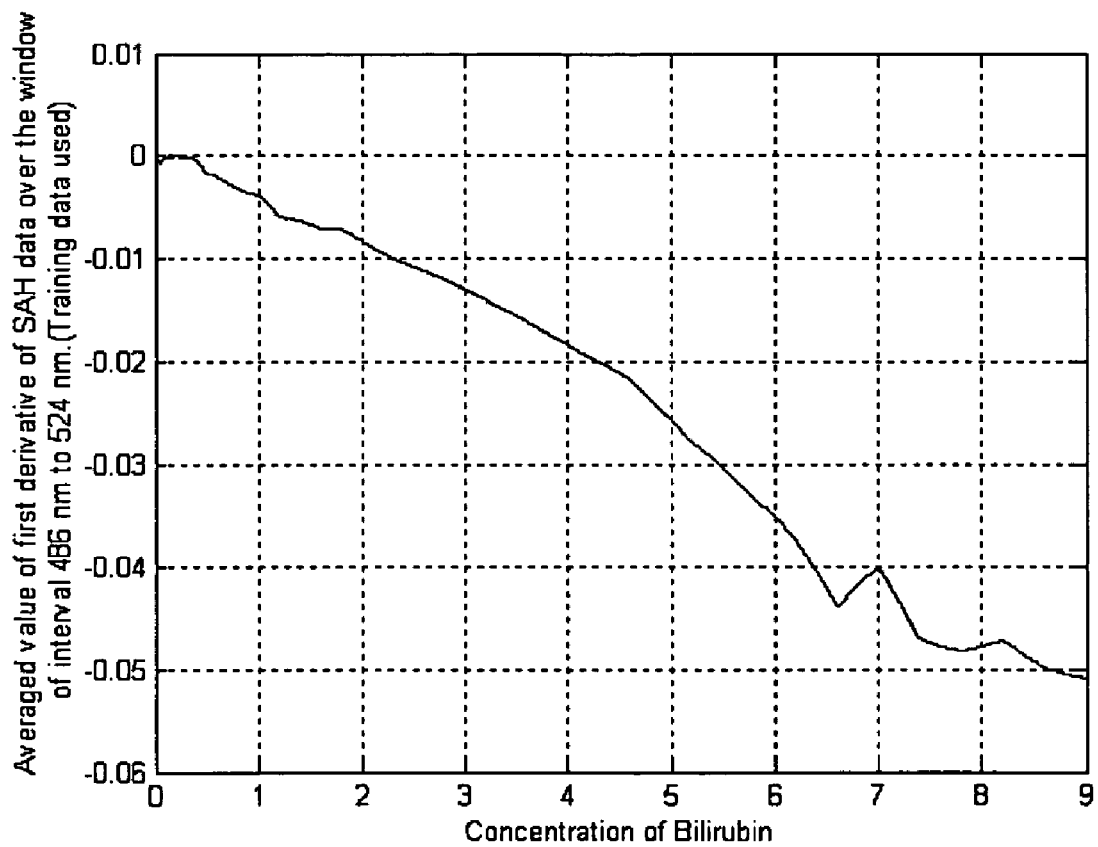
FIG. 7: The average value of the first derivative of SAH data having a fixed concentration of hemoglobin (4.6 g/dl) and varying amounts of bilirubin.
Figure 8A:
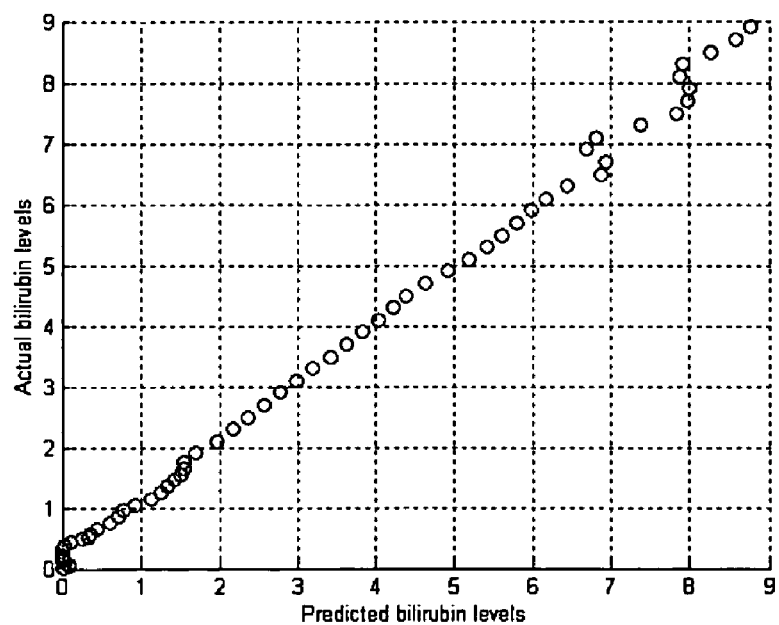
FIG. 8a: The scatter plot between the actual bilirubin level and the predicted bilirubin level.
Figure 8B:
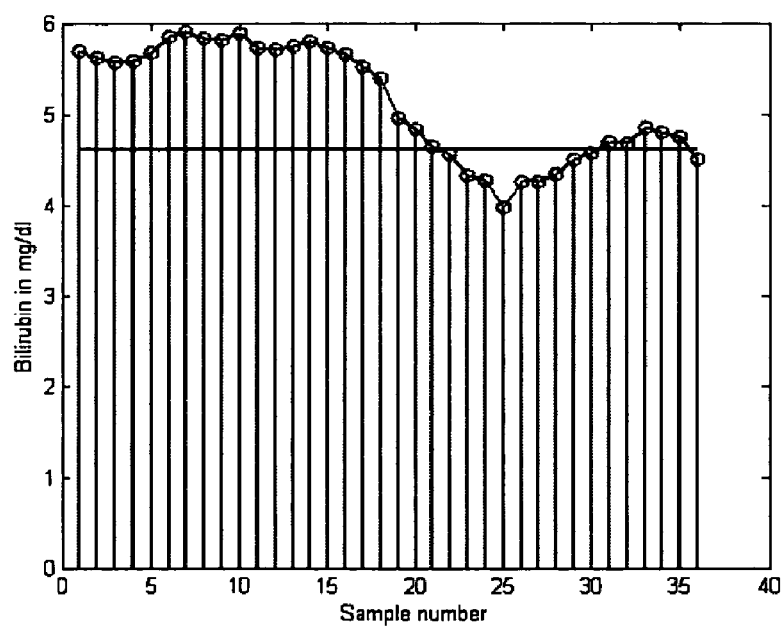
FIG. 8b: Prediction of bilirubin in data where bilirubin remains constant but methemoglobin varies over the range 0 g/dl to 9 g/dl.
Figure 9:
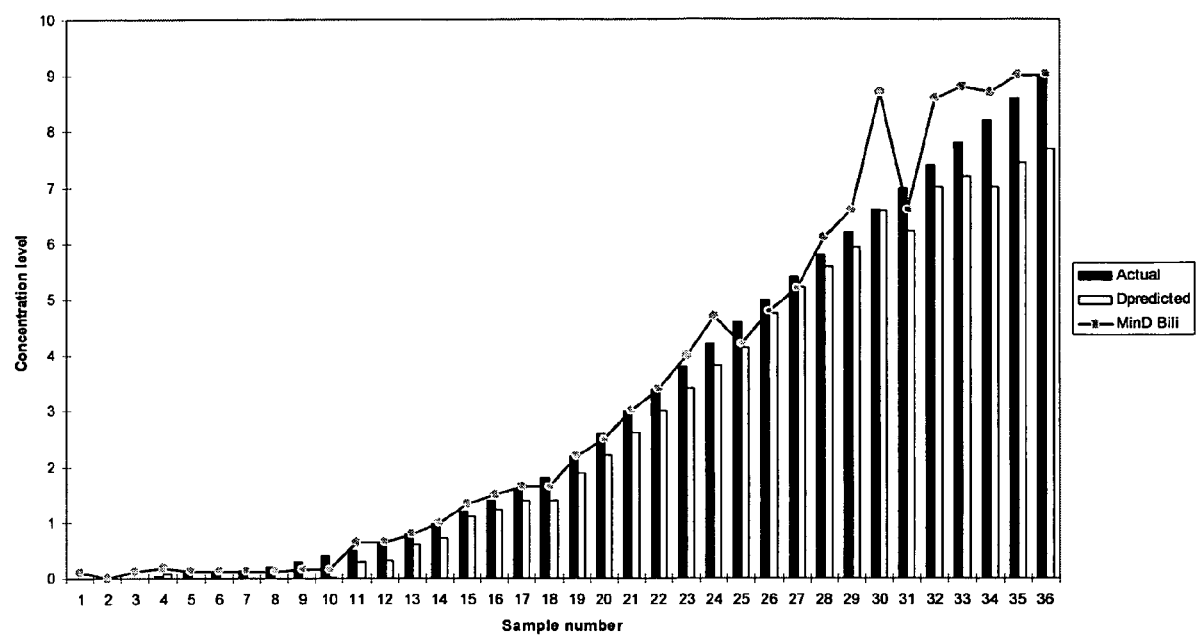
FIG. 9: Prediction of bilirubin in constant methemoglobin (4.6 mg/dl).
Figure 10A:
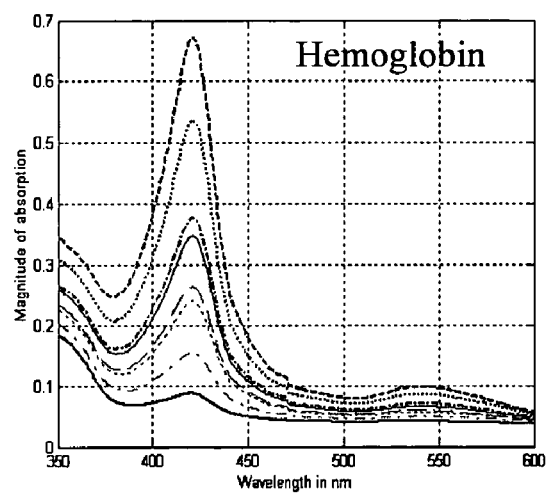
FIG. 10a: Absorption spectra of bilirubin in saline with increasing concentration of bilirubin.
Figure 10B:
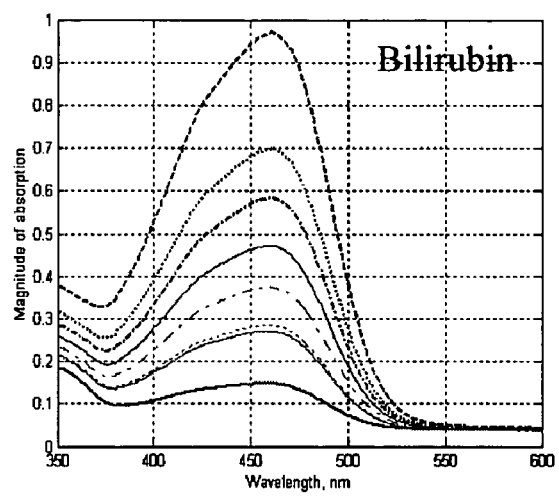
FIG. 10b: Absorption spectra of methemoglobin in saline with increasing concentration of methemoglobin.
Figure 11:
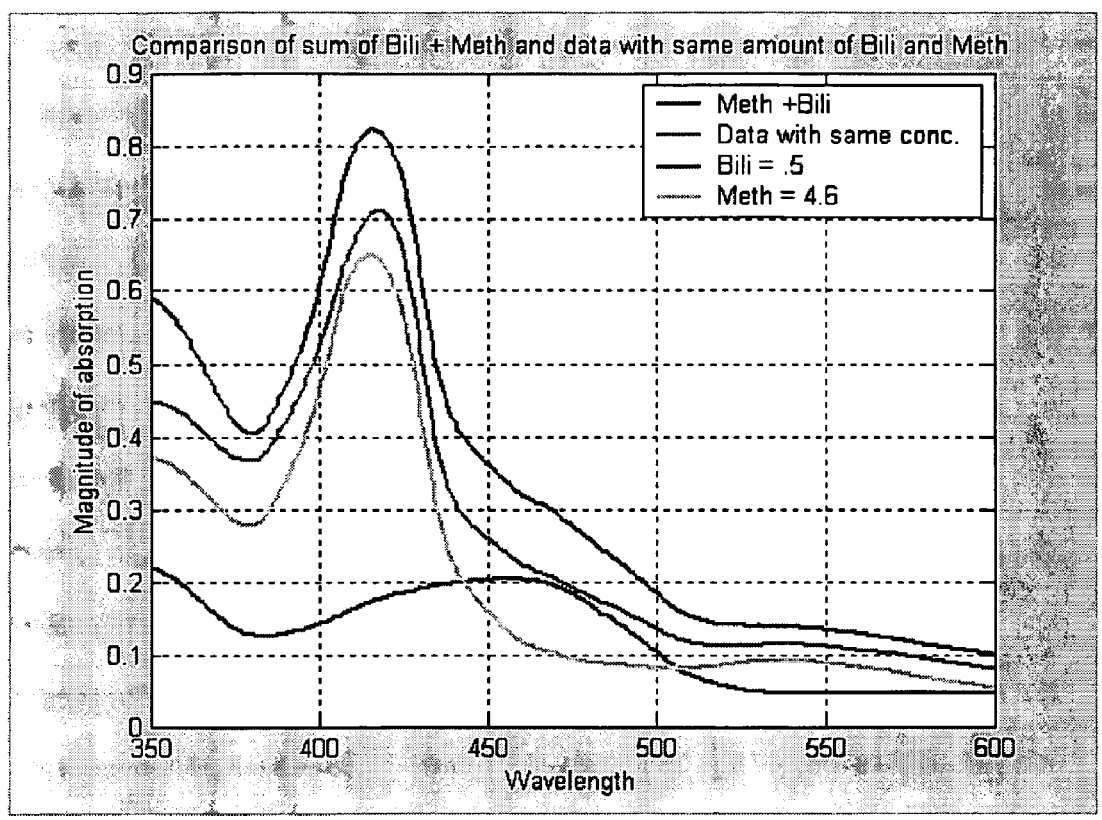
FIG. 11: Sum(n)=M(n)+B(n) varies considerably from the measured SAH(n).
Figure 12:
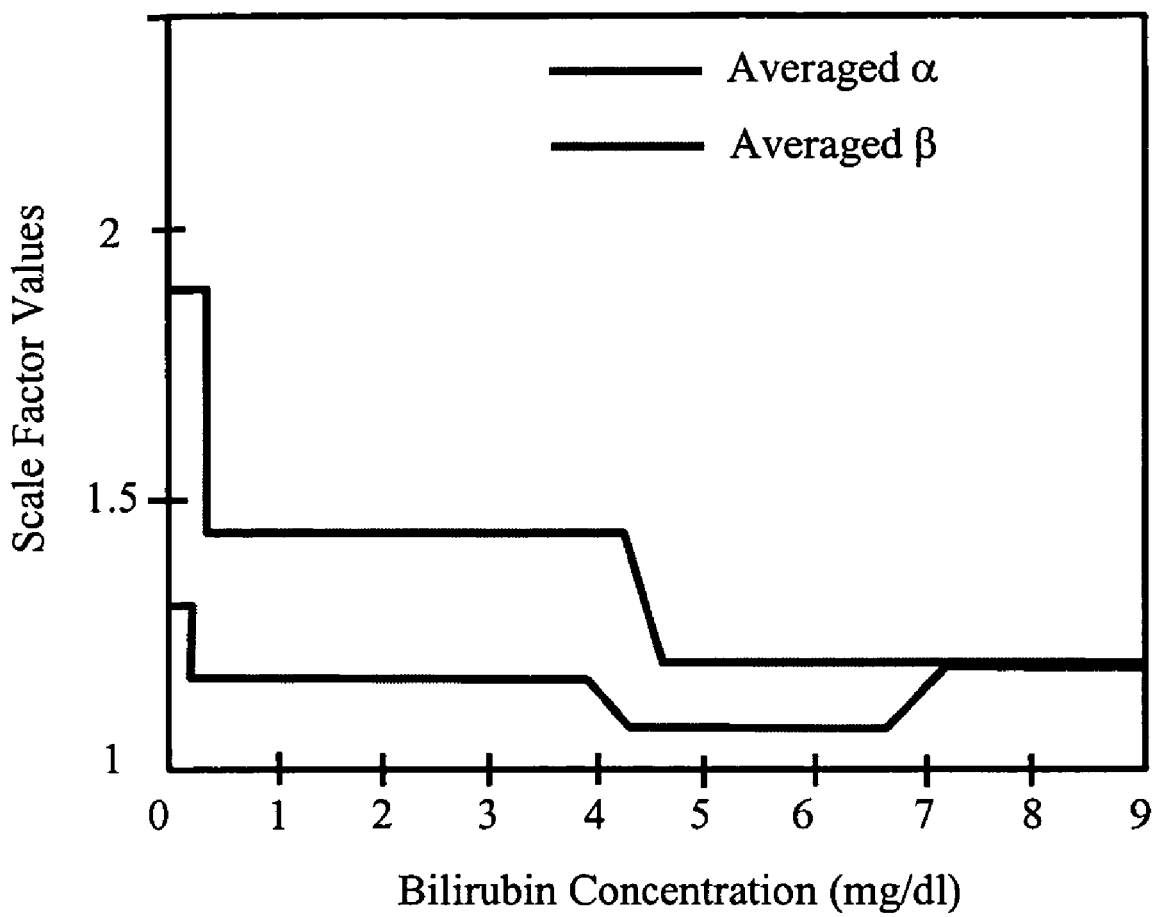
FIG. 12: Scale factor at different concentrations of Bilirubin.

The following acronyms are used throughout the present disclosure.

SAH—Subarachnoid Hemorrhage

Cerebral Aneurysm is a weakened or diseased portion of an artery in brain, rupture of cerebral aneurysm causes a specific type of bleeding in the brain known as Subarachnoid hemorrhage (SAH). When Subarachnoid hemorrhage occurs the brain is often bathed in blood and half the cases of subarachnoid hemorrhage result in fatality.

CSF—Cerebrospinal Fluid

Cerebral spinal fluid is a body fluid that is secreted by the choroid plexus of the ventricles of the brain, and fills the ventricles and subarachnoid part of the brain and spinal cord. CSF acts as a cushion for the brain and regulates the brain's extra-cellular fluid. It also distributes the neuroactive substances in the body and acts as a sink to collect the waste product that is produced by the brain.

LP—Lumbar Puncture

Lumbar puncture or also called spinal tap is the most common method adopted by the medical professionals to collect a specimen of cerebral spinal fluid. The patient is asked to lay on his side with his knees curled up to his abdomen and his chin tucked into his chest. Depending on the patient condition, this procedure is performed with the patient bent in the forward position. The skin is cleaned and a local anesthetic is injected over the lower spine. As the needle is inserted, it's positioned between the third and fourth vertebrae i.e. subarachnoid space, the CSF is drawn from it. After this procedure is completed the patient is asked to remain nearly in a flat position for 8 hours.

CT—Computerized Tomography

Computerized Tomography is a method where cross-sectional images of the human body can be created using x-ray images that are compiled using computer graphics. Generally CT scan is used to analyze brain structures, by narrow beam of X-ray's are passed through the patients head in various angles. This produces different measurements that are fed into a computer graphic program to reconstruct the image of the brain. From the measured attenuation of the rays, the doctor can identify the structure of the body.

RBC—Red Blood Cell

Red Blood Cells also referred as erythrocyte are disc-shaped cells that carries oxygen to the tissues by binding oxygen to hemoglobin. Red blood cells contain a large amount of special red colored molecule called hemoglobin whose function is to pick up oxygen from areas where they are abundant and release it in tissues where the concentration is lowest. Red blood cells are produced in the bone marrow and broken down in the spleen and have a life span of approximately 120 day.

LSR—Least Squares Regression.

If a scatter-plot shows a linear relationship between two quantitative variables, least squares regression is a method for finding a line that summarizes the relationship between the two variables, at least within the domain of the independent variable, x. The least-squares regression line is a mathematical model for the data.

PCA—Principal Component Analysis
Principal component analysis (PCA) involves a mathematical procedure that transforms a number of (possibly) correlated variables into a (smaller) number of uncorrelated variables called principal components. The first principal component accounts for as much of the variability in the data as possible, and each succeeding component accounts for as much of the remaining variability as possible.
PCR—Principal Component Regression
The Principal Component Regression method combines the Principal Component Analysis (PCA) spectral decomposition with a Least Squares (LS) regression method to create a quantitative model for complex samples. Unlike quantization methods based directly on Beer's Law which attempt to calculate the absorbativity coefficients for the constituents of interest from a direct regression of the constituent concentrations onto the spectroscopic responses, the PCR method attempts to regress the concentrations on ~the PCA scores.
PLS—Partial Least Squares
Research in science and engineering often involves using controllable and/or easy to measure variables (factors) to explain, regulate or predict the behavior or other variables (responses). In many applications, researchers are often faced with many variables with ill-understood relationship, the object merely being able to construct a good predictive model to predict the response. Partial least squares (PLS) is a method for constructing predictive modeling when the factors are many and highly correlated. The emphasis using PLS is on predicting the responses and not necessarily on understanding the underlying relationship between the variables (factors).
ANN—Artificial Neural Networks
Artificial neural networks are collections of mathematical models that emulate some of the observed properties of biological nervous systems and draw on the analogies of adaptive biological learning. The key element of the ANN paradigm is the novel structure of the information processing system. It is composed of a large number of highly interconnected processing elements that are analogous to neurons and are tied together with weighted connections that are analogous to synapses.
UV—Ultra-Violet
Ultraviolet or UV light has shorter wavelengths in the electromagnetic spectrum than visible light. For example the sun emits a number of electromagnetic light spectrum, but it is ultraviolet waves that are responsible for causing our sunburns and other skin problems.
IR—Infra-Red
Infrared radiation or IR light is an invisible electromagnetic radiation that has a longer wavelength than visible light. It is generally detected most often by its heating effect. For example IR radiation is used for in space applications.

The present invention contemplates the use of spectrophotometers. This technology is based on firmly established and well-understood optical principles. Spectrophotometry is a technique used for the detection of various molecular or chemical species present in a solution when performing fluid/solution analysis. It involves the measurement of light absorbed in a fluid/solution by analyzing information on the absorbance/transmittance of various compounds at discrete wavelengths. The basic function of a spectrophotometer is to calculate the absorbance/transmittance of light for specific solution. The primary factor responsible for the operation of a spectrophotometer is how well it absorbs light at certain wavelengths. When the transition energy of a molecule matches the incident photon energy at a particular wavelength it results in a process of absorption. This produces an electron excitation from a lower orbital state to a higher orbital state. The variation of absorption/transmission with wavelength is very helpful for the characterization and quantization of various biological and chemical species. Detection of the type of compound is determined by comparing the measured spectra to the reference curves. Bilirubin and hemoglobin have maximum absorbance in the UV to visible range regions.

Absorbance is the basic criterion for determining the concentration changes, but the measuring parameter is transmittance. Therefore, in most spectrophotometric experiments, only the transmittance is measured and converted into absorbance. To reduce error readings, only the absorption at peak wavelengths are considered. In CSF analysis, the wavelength range from 350 to 600 nm is scanned to obtain an entire range of spectra for a specific concentration.

Spectroscopic analysis of human spinal fluid may be diagnostic of hemorrhagic stroke, trauma and traumatic spinal tap. Those skilled in the art will be familiar with related applications of this technology to embodiments including, but not limited to, the diagnosis of infection, meningitis, and neurodegeneration. Accordingly, the inventors have determined a method for objectively analyzing blood in a CSF sample. Within the scope of the present specification, "analyzing" means determining quantitative characteristics, i.e., not merely determining qualitatively the presence or absence of blood in the CSF. Thus, "analyzing" includes determining the amount of blood in the CSF, the relative concentrations of metabolites, herein referred to as "analytes" when subject to analysis, in the CSF and/or the length of time the blood has been in the CSF, among other quantitative determinations. Practioners of the art will appreciate that the metabolites of blood include, inter alia, bilirubin and hemoglobin, and that hemoglobin is comprised of some ratio of methemoglobin, oxyhemeglobin and deoxyhemeglobin.

Specifically, the detection of an SAH can be accomplished using the characteristic spectral absorption patterns for blood's breakdown products. A model of SAH based on these breakdown products has been created and certain spectrophotometric analytical techniques applied. In one embodiment, a modified minimum distance algorithm is used for estimating bilirubin in CSF, which accounted for biological interactions, from the spectrographic data. The current invention also provides a derivative analysis method for analyzing the spectrographic data.

The concentration of bilirubin in CSF/SAH is significant to differential diagnosis of an SAH. A 'low level' of bilirubin indicates that a patient does not suffer from a ruptured cerebral aneurysm. Beyond 1 mg/dL, the patient may be classified with a probable case of SAH. The 'moderate region' is the critical region since it will determine whether or not a patient is classified as suffering from SAH. Beyond 4 mg/dL of bilirubin, a patient is certain of having a ruptured cerebral aneurysm (SAH) and beyond 6 mg/dL indicates a critical condition.

The invention is directed to methods for assessing a condition in an individual. The methods comprise the steps of obtaining a cerebrospinal fluid sample from an individual and analyzing the blood in the cerebrospinal fluid sample. The condition is thereby assessed. One skilled in the art will appreciate the various conditions which may be assessed by analyzing CSF. The conditions include, but are not limited to, stroke, head injury, hemorrhage including subarachnoid hemorrhage, surgical complications including traumatic spinal tap, arterial malformation, venous malformations, tumor, or a combination thereof. In one embodiment, the course of therapy for the condition is assessed. In another embodiment, a therapy for the condition is designed.

One skilled in the art will appreciate that there are many methods for analyzing blood in a CSF sample, any of which may be employed herein. In one embodiment, the blood in a CSF sample is measured by a spectrophotometer. Moreover, one skilled in the art will appreciate that a spectrophotometer generates an output signal over a spectral wavelength range which may be constructed into an absorption versus wavelength curve, herein referred to as a spectral absorption curve. A spectrophotometer may generate the output signal over many different wavelength ranges, and one skilled in the art will appreciate that there are many wavelength ranges relevant to measuring the blood in a CSF sample, any of which may be employer herein. In one embodiment, the spectroscopic wavelength range is from 350 to 650 nm. In a further embodiment, the spectroscopic wavelength range is from about 450 to about 500 nm or from about 390 to about 420 nm, or both. In yet another embodiment, the wavelength range is from about 486 to about 523 nm.

The analysis of the CSF sample may be used to determine the concentration of analytes and/or contaminants in the sample. One skilled in the art will appreciate the various analytes which are found and may be measured in the CSF sample. Further, one skilled in the art will appreciate the various methods for measuring analytes in a CSF sample, any of which may be employed herein. In one embodiment, the analytes in the CSF sample to be analyzed comprise methemoglobin, oxyhemoglobin, bilirubin, or a combination thereof. In a very specific embodiment, bilirubin is an analyte and methemoglobin is a contaminant. In a further embodiment, the analytes are analyzed by spectroscopy. In another embodiment, the concentration of methemoglobin, oxyhemoglobin, bilirubin or a combination thereof is determined from a mathematical algorithm applied to the spectral absorption data. In specific embodiments the mathematical algorithm comprises a linear regression algorithm, a modified minimum distance algorithm, a first or second derivative algorithm or some combination thereof.

The modified minimum distance method is based on the assumption that a spectral absorption curve of a fluid is merely the sum of its component spectral absorption curves. For example, CSF-SAH would be the sum of methemoglobin and bilirubin. However, due to presence of proteins, lipids and other blood components, as well as the inherent non-linearity present in the mixing of two fluids, SAH is actually a complex non-linear summation of methemoglobin and bilirubin. Over small ranges of concentration, levels of methemoglobin and bilirubin and over specific wavelength regions SAH may be approximated as their linear sum by the use of scale factors.

The scale factors vary and depend on the concentration levels of bilirubin and methemoglobin. Only over small concentration regions of bilirubin and methemoglobin can one set of scale factors ($\alpha$ and $\beta$) be chosen. Broader ranges of analyte concentration may require the implementation of multiple scaling factors. One skilled in the art will appreciate the multiple analytes and combinations of scaling factors that may apply thereto. Wavelength regions are chosen for each constituent where its spectrum is dominant and thus provides a high SNR. After computing the appropriate scale factors for the data, the algorithm computes methemoglobin by the minimum distance method, choosing the methemoglobin curve which provides the closest fit among a database of such curves at various concentrations and subtracts that from the original SAH data and then computes the bilirubin value by choosing the bilirubin curve which provides the closest fit amongst curves at all concentration of bilirubin. The process goes on iteratively, until it converges to some methemoglobin curve and bilirubin curve. It has been found that the algorithm provides better estimate of bilirubin in SAH than methemoglobin since the bilirubin spectrum provides higher SNR over the 450 nm to 500 nm wavelength region at all concentration levels.

One inventive method embodiment employs the minimum distance algorithm to estimate a concentration of an analyte in a fluid comprised of the analyte and a contaminant. The method comprises: (a) using a spectrophotometer to generate at least one standard spectral absorption curve for the analyte; (b) using a spectrophotometer to generate at least one standard spectral absorption curve for the contaminant; (c) computing a sum spectral absorption curve ($F_{sum}$) for the fluid by adding the spectral absorptions curves generated in steps (a) and (b); (d) comparing the spectral absorption curves generated in steps (a) and (b) to determine a wavelength range wherein the analyte dominates and a wavelength region wherein the contaminant dominates; (e) obtaining a sample of the fluid and generating a measured spectral absorption curve (F) of the sample over each wavelength range determined in step (d); (f) computing a scaling factor, $\alpha$, for the wavelength range where the anlayte dominates and computing a scaling factor, $\beta$, for the wavelength range where the contaminant dominates and applying the scaling factors such that a scaled spectral absorption curve of the fluid, $F_{sc}$, results and $F_{sc}=\alpha F$ over the wavelength range where the analyte dominates and $F_{sc}=\beta F$ over the wavelength range where the contaminant dominates; (g) optionally, generating at least one interpolative curve from the standard spectral absorption curves generated in steps (a) and (b); (h) using a modified minimum distance algorithm to select which standard contaminant spectral absorption curve of the contaminant is closest in distance to $F_{sc}$ over the wavelength range where the contaminant dominates; (i) computing a residual curve over all measured wavelengths; (j) using a modified minimum distance algorithm to select which standard analyte spectral absorption curve is closest in distance to the residual curve over the wavelength range where the analyte dominates; (k) computing a new residual curve over all measured wavelengths; and (l) iteratively repeating steps (h)-(k) until a standard contaminant curve and a standard analyte curve are selected in consecutive iterations.

In an additional aspects of this method embodiment the fluid comprises cerebral spinal fluid. In a further aspects, the analyte comprises bilirubin and/or the contaminant comprises methemoglobin. In additional aspects the wavelength range where the bilirubin dominates is from about 450 to about 500 nm, and the wavelength range where the methemoglobin dominates is from about 390 to about 420 nm.

The modified minimum distance method has relatively high computation requirements. Well over a hundred standard curves of bilirubin and methemoglobin over a given wavelength range may need to be generated. For the algorithm to be effective over a wide range of bilirubin and methemoglobin concentration a large number of standard curves need to made available while running it.

Derivative spectral analysis of the absorption spectra is useful to improve the selectivity of spectrophotometric determination in multiple components sample, and reduces the computational requirements. One of the major advantages of applying the first spectral derivative analysis technique is that it diminishes the background absorbance in the sample contributed by proteins, lipids, and other blood components which do not have significant absorption peaks within the wavelength of interest. Another important advantage of the derivative spectral analysis technique is that it can separate two overlapping spectra with somewhat Gaussian-like peaks quite effectively. Fortunately, the spectral characteristics of bilirubin and methemoglobin do match to some extent the above stated requirements of derivative spectral analysis.

An additional method embodiment employs the derivative analysis algorithm for estimating a concentration of an analyte in a fluid comprised of the analyte and a contaminant. The method comprises: (a) using a spectrophotometer to generate a standard spectral absorption curve at each of at least two known concentrations of the analyte and at each of at least two known concentrations of the contaminant; (b) computing a first derivative curve of the standard spectral absorption curves generated in (a); (c) inspecting the first derivative curve of the contaminant to determine a wavelength range wherein an average value of the first derivative curve over that range approximates zero; (d) using a spectrophotometer to generate a standard spectral absorption curve for each of at least two samples of the fluid over the wavelength range determined in step (c), wherein each sample of the fluid comprises a different known concentration of the analyte and a known fixed concentration of the contaminant; (e) generating a first derivative curve for each of the standard spectral absorption curves generated in step (d) and computing an average value of the first derivative for each of the at least two samples of the fluid over the wavelength range determined in step (c); (f) generating a curve by plotting the different known concentrations of the analyte from step (d) versus the average values of the first derivatives from step (e); (g) fitting a polynomial equation to the curve generated in step (f), wherein the polynomial comprises coefficients; (h) obtaining a sample of the fluid, using a spectrophotometer to generate a spectral absorption curve over the wavelength range determined in step (c), computing a value for the average first derivative over the wavelength range, plugging that value into the polynomial equation from step (g), wherein the result is the estimated concentration of the substance in the sample of the fluid.

Additional aspects are directed to embodiments utilizing the derivative analysis algorithm wherein the fluid comprises cerebral spinal fluid. Further aspects are directed to this method embodiment wherein 33 wherein the analyte comprises bilirubin, and/or the contaminant comprises methemoglobin. In other aspects the significant wavelength range is from about 486 to about 524 nm.

An additional embodiment employs a statistically-based algorithm to process the signal output to substantially resolve the signal-noise separation problem between in a spectral analysis of a composition comprising analyte (generates signal) and contaminant (generates noise). This method is based on the premise that a statistical relationship exists between the shape of the sum absorbance curve and the respective concentrations of analyte and contaminant. Hence, once the shape of the absorbance curve and the concentration of contaminant are known, the concentration of analyte can be determined from that relationship. First, a data set from standard body fluid solutions of known concentrations of analyte and contaminant are created. In addition, different measurements for known concentrations of a sample are analyzed to predict the instrument and human error to incorporate into the algorithm. A spectrophotometer is used to generate an output signal for the varying known concentrations and standard CSF. A first wavelength range is chosen so that the spectral absorbance curves of both the analyte and contaminant actively contribute, and a second wavelength range is chosen where only one of the two is significant. The algorithmic step is used to estimate the contaminant concentration by considering the contribution of the analyte to the standard body fluid absorption spectrum as a bias in the defined range. A least squares linear fit is obtained between the concentration of contaminant and the average value of the absorption of standard body fluid over the first wavelength range. A linear regression for the contaminant is calculated. Then the analyte concentration in the second wavelength range is estimated. The standard body fluid absorbance spectra is the input into the contaminant regression model and the output is an estimated contaminant concentration value. The estimated contaminant concentration value and the standard body fluid absorbance value are the input into the analyte regression model, and the final output is the estimated value of analyte.

The linear regression model provides a further method for estimating a concentration of an analyte in a fluid comprised of the analyte and a contaminant, and, optionally, EDTA. One embodiment of the method comprises: (a) formulating at least two mock CSF compositions wherein each mock CSF composition has a different known concentration of the analyte and the contaminant; (b) generating a spectral absorption curve for each mock CSF composition; (c) generating an average mock CSF absorption spectral curve, wherein the curve has a shape; (d) determining a first wavelength range wherein both the analyte and the contaminant contribute significantly to the shape of the absorption curve; (e) determining a second wavelength range wherein contribution to the shape of the absorption curve by the analyte is minimal. (f) plotting concentrations of the contaminant versus mean of absorbance across the second wavelength range and using linear regression to generate a contaminant regression model; (g) generating an analyte regression model over the first wavelength; collecting a sample of CSF having unknown concentrations of analyte and contaminant; (h) generating a spectral absorption curve for the sample of CSF; (i) determining an estimated concentration of the contaminant using the contaminant regression model; and (j) entering the estimated concentration of the contaminant into the analyte regression model to generate an estimated concentration of the analyte.

Additional specific embodiments employing the linear regression analysis algorithm are also provided. In a specific embodiment, the fluid comprises cerebral spinal fluid. In more specific embodiments, the analyte comprises bilirubin, and/or the contaminant comprises methemoglobin. In very specific embodiments, the first wavelength range is from about 450 to about 500 nm, and/or the second wavelength range is from about 500 to about 600 nm.

The presence of bilirubin in the CSF relies upon the production of the heat-shock protein heme-oxygenase-1 (HO-1). Detection of elevated bilirubin in CSF is an indicator of erythrocyte catabolism and a robust mechanism for differentiating an SAH from a traumatic spinal tap. Bilirubin production has been determined to require 12 hours. This time lag is likely caused by induction of HO-1 and is not problematic clinically because it occurs during the ultra-sensitive phase of a CT scan's ability to detect an SAH. The bilirubin production lag provides the value of analyzing bilirubin concentrations as indicators of an SAH. Blood introduced during a traumatic tap will not have sufficient time for the catabolic conversion to bilirubin.

A potential pitfall in the clinical usefulness of a bilirubin assay to detect an SAH is the interference caused by hemoglobin concentrations exceeding 0.28 g/dL. It was discovered that the spectroscopic measurement of bilirubin is masked by the presence of hemoglobin. This masking is not due to noise of the hemoglobin signal but rather interference from the hemoglobin. The bilirubin is binding to hemoglobin and that this binding alters bilirubin's spectroscopic absorbance characteristics. These binding properties cause the spectral curve of bilirubin, when added to hemoglobin, to be non-linearly dependent upon the concentration of hemoglobin. This discovery is unexpected because hemoglobin has never been found to be a bilirubin binding protein. The specific binding of bilirubin drastically alters the precision with which the state of the art technologies can detect and quantify bilirubin. The binding constants may be used to optimize and improve the algorithm. Without incorporating these binding constants into an algorithm calculation one would produce a systematic error with state of the art technologies. One embodiment of the invention utilizes a chemical to increase the threshold, thereby enhancing the output signal. A more specific embodiment of the present inventive methods utilizes an EDTA extraction to enhance the signal. It will be apparent to one of ordinary skill in the art that other chelating agents and chemicals may be selected to provide a similar enhancing effect and the present inventive methods should not be construed as limited to the selection of EDTA.

Studies have determined that bilirubin's concentration depends upon the initial volume of hemorrhage. In addition, the concentration of bilirubin in the CSF increases with time. Together these two aspects of metabolism may allow identification of both the volume and timing of an SAH.

The analysis of the cerebrospinal fluid sample therefore may be used to determine a length of time the blood has been in the cerebrospinal fluid. In one embodiment, the length of time the blood has been in the cerebrospinal fluid correlates with the concentration of analytes in the cerebrospinal fluid sample. One skilled in the art will appreciate the various assessment which may made based upon the length of time the blood has been in the cerebrospinal fluid, any of which may be employed herein.

The analysis of the cerebrospinal fluid sample may also be used to determine the amount of blood in the cerebrospinal fluid sample. The determination of the amount of blood in the cerebrospinal fluid sample may be used as a correlation of the severity of the condition.

The method of assessing a condition in an individual may further comprise the step of obtaining sequential cerebrospinal fluid samples from the individual. These sequential samples may be used to assess severity of the condition or efficacy of treatments.

One inventive embodiment is directed to an instrument for rapidly assessing a condition of an individual by estimating a concentration of an analyte in a body fluid of the individual. The instrument comprises: a device for analyzing a body fluid of the individual, wherein the device receives a sample of the body fluid and generates an output signal; and a processor which subjects the output signal to an algorithm which yields an estimated value of the concentration of the analyte.

In more specific aspects of this embodiment, the algorithm comprises a linear regression algorithm, a modified minimum distance algorithm, a derivative analysis algorithm, or some combination thereof. In a very specific embodiment the algorithm comprises a derivative analysis algorithm. In another very specific embodiment the algorithm comprises a modified minimum distance algorithm, and in a further very specific embodiment the algorithm comprises a linear regression algorithm. In other specific embodiments, the body fluid comprises cerebral spinal fluid. In a more specific embodiment, the condition assessed is whether the patient has suffered a subarachnoid hemorrhage. In a further embodiment, the analyte is bilirubin. In one embodiment the instrument is portable.

The following Examples further illustrate particular embodiments of the invention.

The specific embodiments in the examples described herein are illustrative in nature only and are not intended to be limiting of the claimed compositions, methods or articles. Additional embodiments and variations within the scope of the claimed invention will be apparent to those of ordinary skill in the art in view of the present disclosure.

EXAMPLE 1

This example illustrates the use of the inventive methods to perform a differential diagnosis the spectrophotometer output provides the spectral content of the CSF obtained from LP. Generally, due to the rupture of a blood vessel while performing LP, the spectral content would consist of hemoglobin and bilirubin. The hemoglobin consists of two different components: oxyhemoglobin and methemoglobin. However, within a short period of time, the oxy-hemoglobin gets converted into methemoglobin. Therefore, the primary objective is to detect the presence of bilirubin in CSF-SAH. In addition to bilirubin (the concentration of which depends on the extent of aneurysm rupture), CSF-SAH may have methemoglobin and certain other proteins in it. A measured spectral output for SAH was generated and CSF/SAH with two different concentrations of bilirubin were plotted. It was observed that absorption increased over all wavelength ranges for the higher bilirubin concentration but was more pronounced in the region between 450 and 500 nm.

Since the CSF/SAH data consists of methemoglobin and bilirubin, analysis of their individual spectra is essential in finding a detection procedure for bilirubin. The individual spectra of methemoglobin and bilirubin in saline were obtained from spectrophotometer analysis. The absorption of bilirubin was found to be much higher than methemoglobin between the wavelength regions of 450-500 nm, while the absorption of methemoglobin dominated over bilirubin over the wavelength region 390-420 nm. These differences provide a basis for differentiating between bilirubin and methemoglobin in CSF-SAH. Pre-measured spectral curves of bilirubin and methemoglobin in saline were generated at different concentrations. Those curves formed the basis for estimating the concentrations of bilirubin and methemoglobin in the laboratory measured sample of CSF-SAH.

EXAMPLE 2

This example illustrates the calculation of scaling factors in the development of the minimum distance method algorithm employed in some embodiments of the inventive methods.

The performance of the algorithm depends on the ability to describe the measured SAH spectrum accurately as the linear combination of pre-measured bilirubin and methemoglobin spectra over the wavelengths of significance, i.e., between 390 and 420 nm and 450 to 600 nm. Therefore, over a certain set of wavelengths in the spectral data, we adjust the SAH curve with a scale factor $$S(n) = \alpha * SAH(n) \approx (B(n) + M(n)) \quad 390 \leq n \leq 420 \quad (1)$$

$$S(n) = \beta * SAH(n) \approx (B(n) + M(n)) \quad 450 \leq n \leq 500 \quad (2)$$

where, $\alpha$ and $\beta$ are scaling factors which are computed by minimizing the least squares (LS) error functions $$\epsilon_i^{(1)} = \Sigma \|(\alpha \cdot SAH_i(n) - (M_i(n) + B_i(n))\|^2 \quad 390 \leq n \leq 420 \quad (3)$$

$$\epsilon_i^{(2)} = \Sigma \|(\beta \cdot SAH_i(n) - (M_i(n) + B_i(n))\|^2 \quad 450 \leq n \leq 500 \quad (4)$$

such that the scaled SAH curve and the sum curve are nearly equal over the wavelengths indicated.

A set of solutions is prepared in which methemoglobin is constant at 4.6 g/dL in each but bilirubin is varied from 0 to 9 mg/dL. The optimum scale factors for each set of concentrations is determined. Actual scale factors are calculated at each concentration over the wavelengths of significance and the average value of the scale factors in different wavelength regions are calculated to use in the program to reduce the amount of computation. The optimum scaling factors for different concentrations of bilirubin change as the concentration of methemoglobin changes. Hence, the scaling factors, $\alpha$ and $\beta$, at different concentrations of bilirubin and methemoglobin need to be computed initially so as to produce minimum error with laboratory data. These scaling factors, once generated, would then be used as described in (1) and (2). The generation of scaling factors at different concentrations of methemoglobin and bilirubin can be described by a "Bilirubin/Methemoglobin (B/M) concentration plane" which is a grid array of increasing concentrations of bilirubin versus increasing concentrations of methemoglobin with the corresponding scale factor pairs in each grid of the array representing different concentration regions. [refer to a Fig.]

While FIG. 13 shows the bilirubin/methemoglobin (B/M) concentration plane divided into regular square regions, each with its own set of scale factors, in reality the partitioning of the B/M plane for the optimum scale factors may not produce such regular regions. While performing simulations with test data, the scale factors of the shaded region in the center of the B/M plane are the ones chosen initially. This means the initial assumption is that the bilirubin/methemoglobin concentration lies within this region. Using the scale factors corresponding to this region, the algorithm is used to form estimates of the concentration of methemoglobin and bilirubin in an SAH sample. However, after one iteration of the algorithm the results may lead us away from the center grid of the B/M plane. For example, the computed bilirubin and methemoglobin concentrations may place it in the $\alpha_{24}$ and $\beta_{24}$ region of the B/M plane and not the center $\alpha_{33}$ and $\beta_{33}$ region as initially assumed. Hence, the algorithm is invoked again but uses $\alpha_{24}$ and $\beta_{24}$ as the new scaling factors. The process is continued until the bilirubin and methemoglobin concentration converges to a specific grid on the B/M plane. All the scale factors on the B/M plane, as shown in FIG. 13, are pre-computed using the method as described in (3) and (4) and shown in FIG. 13. Partitioning the B/M plane into greater number of grid regions could lead to higher accuracy at a higher computational cost.

EXAMPLE 3

This example provides results of estimating bilirubin and methemoglobin in a measured CSF/SAH solution using the minimum distance method.

First, M (n) and B (n) were estimated in a sample with constant methemoglobin and increasing bilirubin. Spectral curves for 36 different concentrations of methemoglobin and bilirubin were measured in the laboratory, 105 additional curves were interpolated from those as discussed previously. The methemoglobin concentration was held constant at 4.6 g/dL while the bilirubin concentration was increased from 0 mg/dL to 9 mg/dL. The bilirubin concentrations were not uniformly distributed over the entire concentration range. Since the lower and middle levels on the concentration scale are more critical in terms of diagnosis of SAH, the number of concentrations of bilirubin measured in this region is higher. This helps us test the algorithm more rigorously over the critical concentrations of bilirubin.

The results indicate that the estimation error for bilirubin is lower than that of methemoglobin. The magnitude of absorption in the region between 390 and 420 nm increases strongly for bilirubin with increasing concentration. This region is therefore used for estimating methemoglobin by the minimum distance method. However, the scaling factor equation becomes less exact as the concentration of bilirubin increases and exhibits considerable absorption over 390-420 nm which leads to lower methemoglobin estimates than their true value. A lower estimate of methemoglobin leads to a higher estimate of bilirubin than its true value. However, this is no reason for concern. Bilirubin levels beyond 6 mg/dL represents a critical condition. From the figures, we find that significant error in bilirubin estimation occurs beyond 6.6 mg/dL using the algorithm on this set of laboratory data. Consequently, the bilirubin estimate is higher than its true value of 6.6 mg/dL, and we would still classify the patient as being in a critical state. At a lower concentration of bilirubin, when accurate estimation of bilirubin level is much more critical for diagnosis of a SAH condition, the algorithm produces negligible error and is highly accurate. A second set of results of estimating bilirubin and methemoglobin in CSF/SAH solution using the minimum distance method were produced. Again, 141 spectral curves were used (36 measured, 105 interpolated). Unlike the previous example, the bilirubin concentration is held constant at 4.6 mg/dL in all SAH samples, while the methemoglobin concentration is increased from 0 mg/dL to 9 mg/dL. With increasing concentration, the absorption by methemoglobin in the wavelength region 450-500 nm does not exhibit any considerable increase. Hence, an increasing concentration of methemoglobin does not have a detrimental effect on estimating bilirubin. The estimation error for bilirubin is lower than that of methemoglobin. The largest error in methemoglobin estimation is 1.5 g/dL which is still much lower than that of the previous case. The maximum error in bilirubin estimation is 0.6 mg/dL.

EXAMPLE 4

This example illustrates how methods comprising the modified minimum distance algorithm are used to estimate the amount of methemoglobin and bilirubin in a measured SAH sample.

A set of standard curves at various concentrations of methemoglobin and bilirubin were produced using the spectrometer experimental setup. These standard curves are used as quantization levels for estimating the bilirubin or methemoglobin values in a CSF/SAH sample. An interpolation method was used to generate additional curves from the standard spectral curves produced in the laboratory. A higher number of curves provide a larger number of quantization levels which results in greater accuracy in determining the methemoglobin and bilirubin concentration levels, even though the interpolated curves may not be as accurate as additional measured curves. In this regard, thirty six standard curves at different concentration of bilirubin and methemoglobin in saline were produced in the laboratory. Additional spectral curves were generated to improve the resolution of the algorithm by interpolating three new curves between each adjacent pair of original spectral curves. Since there were 36 original spectral curves both for methemoglobin and bilirubin in saline (for 36 different concentrations of each), 35×3=105 interpolated curves were generated, thus bringing the number of possible concentrations of methemoglobin and bilirubin to 141. Generally, the performance of the algorithm would be expected to be more accurate with a higher number of standard curves. However, beyond a certain number of curves (such as 141 in this case), the gain in accuracy is often negligible compared to the effort required to produce standard concentration curves in the laboratory and the resulting increase in computations.

The determination of the concentrations of bilirubin and methemoglobin is as follows.

First, choose $$Mi, \text{ such that } \|S(n)-M_1(n)\|_{min}, 390<n<420, 1<i<141 \quad (1)$$

where $M_i(n)$ corresponds to the absorption curve of a concentration (indicated by the index i) of methemoglobin. Using the minimum distance method, then, (1) determines which methemoglobin curve amongst the standard methemoglobin curves is closest in distance (hence, closest fit) to S(n), which is the scaled version of SAH(n) over the specified wavelength region. Then compute the residual curve $$R_M(n)=\|S_{init}(n)-Mi(n)\| 350 \leq n \leq 600 \quad (2)$$

over all of the measured wavelengths which, intuitively, should be a measure of the bilirubin content in S(n). $S_{init}(n)$ denotes the scaled version of SAH(n) being used in the first step of the process. Then, similar to (1), determine the concentration of bilirubin with the following:

$$\text{Choose } B_i, \text{ such that } \|R_M(n)-B_i(n)\|_{min}, 450 \leq n \leq 500,$$
$$1 \leq i \leq 141 \quad (3)$$

Where, $B_i(n)$ corresponds to the absorption curve of a concentration (indicated by the index i) of bilirubin. Equation (3) determines which bilirubin curve, amongst the standard bilirubin curves, is closest in distance to $R_M(n)$, and hence, gives an estimate of the bilirubin concentration in the SAH sample. Then form a new residual that gives a refined measure of the methemoglobin content in the SAH sample according to $$R_B(n)=|S_{init}(n)-B_i(n)| \; 350 \leq n \leq 600 \quad (4)$$

$$S(n)=R_B(n) \; 350 \leq Sn \leq S600 \quad (5)$$

Equation (5) indicates that the new residual is then used in place of S(n) in the algorithm as steps (1)-(5) are repeated. However, $S_{init}(n)$ is not changed in successive iterations of the algorithm. This is because $R_B(n)$ may now be considered as the methemoglobin content in SAH by the same reasoning as in (2) for bilirubin, and hence, a better estimate of methemoglobin is expected by using the minimum distance algorithm between $R_B$ and the standard methemoglobin curves. The remainder $R_M(n)$ in the next iteration still must be computed from the original scaled SAH data, $S_{init}(n)$, since the interest is in estimating bilirubin and methemoglobin in the SAH data. The iterative procedure is continued until $M_i$ and $B_i$ converge, i.e., the same $M_i$ and $B_i$ are chosen in consecutive iterations.

EXAMPLE 5

This example illustrates the application of the inventive methods to the problem of differentially diagnosing a subarachnoid hemorrhage from a traumatic spinal tap. Use of methods comprising the step of processing signal output using the derivative algorithm is specifically illustrated.

The first step involves obtaining CSF from the patient. The fluid is then analyzed using the spectrophotometer and an output signal is generated.

The spectrophotometer output provides an absorption spectral curve of the CSF obtained from LP. Generally, due to the rupture of a blood vessel while performing LP, the spectral content would consist of hemoglobin and bilirubin. The hemoglobin consists of two different components: oxyhemoglobin and methemoglobin. However, within a short period of time, the oxyhemoglobin gets converted into methemoglobin. Therefore, the primary objective is to detect the presence of bilirubin in CSF/SAH. In addition to bilirubin (the concentration of which depends on the extent of aneurysm rupture), CSF/SAH may have methemoglobin and certain other proteins in it. A measured spectral output for SAH with two different concentrations of bilirubin was plotted. It was observed that absorption increases over all wavelength ranges for the higher bilirubin concentration but is more pronounced in the region between 450 and 500 nm.

Absorption spectra of methemoglobin and bilirubin at concentration levels of 2.2 g/dl and 0.6 mg/dl were generated. The peak of methemoglobin absorption occurs around 413 nm while that of bilirubin occurs at 460 nm. The first derivative of the absorption spectral curves was calculated and it was observed that the first zero crossing of the Methemoglobin data occurs around 413 nm, remains negative for a while and then almost steadily fluctuates around the zero axis from 460 nm onwards. Around 460 nm, the first zero crossing of bilirubin data occurs which remains negative until 536 nm. In the region from 460 nm and 536 nm, while the derivative of bilirubin data remains negative, methemoglobin fluctuates about zero. Thus, this region may be used quantitatively to estimate the bilirubin concentration.

The second derivative of the bilirubin and methemoglobin absorption spectral curves was also calculated. In addition, the ratio of bilirubin and methemoglobin over the entire wavelength region using the absorption spectrum was calculated, along with its first derivative and second derivative. The ratio is referred to as a signal to noise ratio (SNR) in this case since bilirubin levels may be considered as the signal and the methemoglobin is the noise which tends to dominate the signal. The wavelength regions of positive SNR are significant. Since higher values of SNR may be considered analogous to better estimation of bilirubin, the first derivative data was deemed to be the most promising as it exhibited reasonably high SNR levels over considerable wavelength regions. The actual absorption spectrum of both of these analytes seems to be least promising with the lowest SNR values.

Absorption spectral curves of solutions containing both methemoglobin and bilirubin were generated. The methemoglobin concentration remains constant in the 36 different solutions while the bilirubin concentration varies from 0 mg/dl to 9 mg/dl. The absorbance spectra shows that, with increasing concentration of bilirubin, the absorbance increases over the entire wavelength region of 350-600 nm, though non linearly. The region of most significant increase is between 450 nm and 500 nm, while beyond 525 nm, the increase in absorbance is insignificant. However, its is not possible to develop a calibration scale using the data, since, with increase in concentration, the absorption of methemoglobin also increases over a similar wavelength region.

EXAMPLE 6

This example illustrates several characteristics of the production of bilirubin from hemoglobin by HO-1 and specifically illustrates that the clinical usefulness of the bilirubin assay to detect an SAH is enhanced by diminishing the interference caused by hemoglobin concentrations exceeding 0.28 g/dL. The example demonstrates that the threshold can be increased to 0.6 g/dL with EDTA hemoglobin extraction. A commercially available assay for bilirubin exists and was modified to reduce interference from hemoglobin. The in vitro production of bilirubin was examined in a system containing blood, CSF and rat choroid plexus as the tissue source for HO-1. In vivo experimentation consisted of both rat and porcine experimental models of SAH. Spectrophotometric analysis was completed by manipulation of absorption curves to reduce hemoglobin's interference and predict bilirubin concentrations from standard component curves.

Hemoglobin above 0.28 mg/dL obscures bilirubin assays and consequently diminishes their clinical usefulness. Ethylenediaminete-traacetic acid (EDTA) was used to partially extract hemoglobin. Stock hemoglobin solutions ranging from 0.15 g/dL to 4.8 g/dL were prepared. Concentrations of hemoglobin were measured using a commercially available hemoglobin assay prior to and after the addition of EDTA solution (1:1 volume). Similarly, bilirubin solutions were prepared in concentrations ranging from 0.04 mg/dL to 6.72 mg/dL. Bilirubin assays were also conducted for each sample before and after EDTA extraction.

The first analysis was conducted in vitro. To examine bilirubin production, CSF, whole blood, and a tissue source of HO-1 were combined. These materials were then incubated at 37° C. for 72 hours with serial assays for bilirubin. Each constituent was also sequentially eliminated and replaced with a volumetric control. This generated one experimental group (1) and three control groups (2-4): (1) 50 uL blood, CSF, and HO-1 (2) CSF, HO-1, and no blood (3) 50 uL blood, no CSF, and HO-1 (4) 50 uL blood, 0.9% sodium chloride, and HO-1. The HO-1 was provided by choroid plexus cells harvested from un-injured Sprague-Dawley rats. Whole arterial blood was collected from the same Sprague-Dawley rat. CSF was collected from a normal patient.

A second analysis was conducted in vivo. Rat and porcine SAH models were used for the in vivo production of bilirubin. In the rat experiments whole arterial non-heparinized blood was collected from the femoral arteries of four Sprague-Dawley rats. The animals were then placed into a stereotactic head frame and their cranio-cervical junction dissected to expose the alanto-occipital membrane. Using microsurgical technique, the cisterna magna was injected with harvested autologous blood with incremental increases in the volume of blood injected (15, 75, 100, and 200 uL). The incisions were then sutured closed and the animals recovered. 24 hours after the injections, the animals were re-anesthetized and re-secured in the stereotactic headframe. The alanto-occipital membrane was re-exposed and CSF collected from their cisterna magna. The CSF was assayed for total bilirubin.

Anesthetized Yorkshire pigs (16-20 kg) were utilized for the porcine model of SAH. The cranio-cervical junction was exposed in each animal, and either blood or saline was injected into their cisterna magna with an 18 gauge spinal needle. In the experimental group, 3 animals were injected with 250 µL of arterial blood. In the control group, 1 animal was injected with 250 µL of 0.9% sodium chloride. For those animals in the experimental arm, whole arterial non-heparinized blood was obtained from their femoral artery. Prior to dissection of the cranio-cervical junction, the lumbar spine at the level of the L4/L5 spinous processes and lamina, as well as the upper sacrum, was exposed. A 22 gauge spinal needle was inserted into the lumbar cistern and CSF collected. Both the cisterna magna and lumbar cistern spinal needles were left in place. CSF was sampled prior to and every hour after the blood/saline injection until 24 hours post-injection. The CSF was centrifuged, and hemoglobin and bilirubin concentrations were assayed. Importantly, the volume of the porcine SAH (250 µL) is a volumetrically equivalent hemorrhage to a low volume rodent SAH described previously.

For the spectrophotometric analysis, CSF from a normal patient was spiked with known concentrations of methemoglobin and bilirubin. Spectrophotometric investigation was accomplished using partial component analysis from standard absorption peaks. The spectrophotometric algorithm was interrogated for its ability to predict the hemoglobin and bilirubin concentrations.

The summary of all available data suggests bilirubin production requires 12 hours. This time lag is likely due to in the induction of HO-1. In fact, bilirubin's production lag provides the value of this diagnostic modality. Blood introduced during a traumatic tap will not have sufficient time for the catabolic conversion to bilirubin. One potential pitfall in the clinical usefulness of a bilirubin assay to detect a SAH is the interference caused by hemoglobin concentrations exceeding 0.28 g/dL. This threshold can be increased to 0.6 g/dL with EDTA hemoglobin extraction.

TABLE 1

| HEMOGLOBIN (g/dL) | | BILIRUBIN (mg/dL) | |
| --- | --- | --- | --- |
| [Hgb] − EDTA | [Hgb] + EDTA | [Br] − EDTA | [Br] + EDTA |
| 0.150 | .07 | 0.040 | .02 |
| *0.28 | 0.13 | 0.32 | 0.16 |
| 0.3 | 0.14 | 0.6 | 0.3 |
| 0.6 | *0.28 | 1.56 | 0.79 |
| 1.2 | 0.56 | 3.24 | 1.64 |
| 2.4 | 1.12 | 4.54 | 2.29 |
| 3.6 | 1.69 | 5.24 | 2.65 |
| 4.8 | 2.25 | 6.72 | 3.40 |

Hemoglobin and bilirubin solutions pre- & post-EDTA extraction.
*Represents the threshold concentration for accuracy of the bilirubin assay.

The in vitro data provides evidence of the requisite constituents for bilirubin production. Elimination of CSF, HO-1 or blood prevents the conversion of hemoglobin to bilirubin. This is clinically advantageous because CSF removed from a patient will no longer be in contact with the membrane-bound HO-1. The in vivo data suggests two clinically applicable aspects of this methodology. First, bilirubin's concentration depends upon the initial volume of hemorrhage. Secondly, the concentration of bilirubin in the CSF increases with time. Together, these two aspects of metabolism may allow identification of both the volume and timing of a SAH.

EXAMPLE 7

This Example Illustrates an Assay of Total Bilirubin in CSF Samples

Total bilirubin was assayed using a method based on those developed by Michaelsson (1961), "Bilirubin determination in serum and urine", Scand. J. Clin. Lab Invest. Suppl. 56 13(1) and Nosslin (1960), "The direct diazo reaction of bile pigments in serum", Scand. J. Clin. Lab Invest. Suppl. 49 12(1), which references are incorporated by reference herein. The method was adapted for use in a microtiter plate.

Blood samples were first assayed for hemoglobin content (Sigma Diagnostics procedure #525, total hemoglobin). If the sample was found to be below 300 mg/dL, the sample was used untreated. If the sample was above 300 mg/dL, but below 600 mg/dL, the sample was diluted 1:1 with saturated EDTA solution and centrifuged to remove 50% of the hemoglobin, which also removes 50% of the bilirubin. The sample could then be assayed for bilirubin as described, accounting for the dilation and predictable loss of bilirubin. If the sample contained more than 600 mg/dL hemoglobin it was deemed unsuitable for bilirubin assay.

The sample (10 µL) was treated with a caffeine/benzoic acid reagent (25 g/L caffeine and 38 g/L sodium benzoate in 85 mM sodium acetate solution) in order to release bound bilirubin thus making all the bilirubin available for the diazotization reaction. Diazo reagent (75 µmoles sulfanilic acid and 6.6 µmoles sodium nitrite dissolved in 6 mL of 0.1 M HCI) was added to yield the pink (at acid and neutral pH) azobilirubin compound. This moiety was then stabilized with a cysteine reagent (100 mg cysteine dissolved in 10.5 mL of $dH_2O$) and alkalinized with alkaline tartrate reagent (100 mg cysteine dissolved in 10.5 mL of $dH_2O$) to yield a blue coloration which is less prone to hemoglobin interference. The blue reaction mixture was analyzed spectrophotometrically at 600 nm, and the samples were compared to a concomitantly run standard curve of Lin-trol® bilirubin prediluted samples (Sigma, St. Louis, Mo.) to determine total bilirubin concentration.

Assay of Total and Direct Bilirubin Using a Diazo Reaction Method

The reaction of bilirubin with diazotized sulfanilic acid to form azobilirubin is well known in the art and was first described in 1981. The resultant derivative of the reaction is colored, pink at acidic and neutral pH, and blue at alkaline pH. The assay measures the blue coloration, as this is more sensitive and minimizes the interference from hemoglobin and hemoglobin derivatives. The present protocol was altered and adapted for use in a microtiter plate.

Materials Required

Flat-bottomed 96 well plates and a spectrophotometric plate reader capable of reading absorbance at 600 nm.

Reagents

Hydrochloric Acid—0.1 M solution, which provides an acidic environment for the diazo reaction and is therefore used as a solvent for the diazo reagent and for the Diazo-free blank.

Diazo reagent solution (Diazotized sulfanilic acid)—75 µmoles sulfanilic acid and 6.6 µmoles sodium nitrite dissolved in 6 mL of 0.1 M HCL. After the solution is made it must be replace if appears yellow or in any case every 7 days. Store in the dark at 4° C. The solution forms a colored ion in direct proportion to the bilirubin concentration.

Cysteine Solution—100 mg cysteine dissolved in 10.5 mL $dH_2O$. Store solution refrigerated at 4° C., and keeps for several months. The solution stabilizes the otherwise labile azobilirubin moiety.

Caffeine Reagent—25 g/L caffeine and 38 g/L sodium benzoate in 85 mM sodium acetate solution. Store solution refrigerated at 4° C., and keeps for two months or discard if precipitate is observed. The solution acts as a accelerant to allow indirect (bound) bilirubin to be diazotized and thus enables measure of total bilirubin.

Alkaline tartrate—350 g/L sodium potassium tartrate in 2.5 M NaOH solution. Store in the dark at 4° C., keeps for 6 weeks or discard if coloration is observed. Alkaline tartrate alkalinizes the azobilirubin reaction and forms blue coloration in direct proportion to the bilirubin concentration which can be measured spectrophotometrically at 600 nm. This avoids interference from hemoglobin or its breakdown products.

Bilrubin standard solutions—available pre-diluted from Sigma (St. Louis, Mo.) as Lin-trol® total and direct preditluted set, catalog number B1153. The standards contain the following amounts of total and direct bilirubin, as assayed by Sigma.

TABLE 2

| LEVEL | Total bilirubin (mg/dL) | Direct bilirubin mg/dL |
|---|---|---|
| 1 | 0.2 | 0.2 |
| 2 | 1.6 | 1.1 |
| 3 | 3.0 | 2.1 |
| 4 | 7.8 | 5.5 |
| 5 | 16.2 | 11.3 |
| 6 | 22.7 | 16.3 |
| 7 | 26.2 | 18.4 |
| 8 | 33.6 | 24.1 |

Microplate (96 Well) Procedure

Although this assay is extremely consistent between batches of reagents and standards, a standard curve for every plate read is run. A blank containing no diazo is plated, as well as blank containing no bilirubin to check for background interference from reagents.

The following Table 3 gives the amounts in µL of each reagent required for the blank, total and direct assays in a 96 well plate, as well as the order in which the reagents should be added.

TABLE 3

| COMPONENT | BLANK | TOTAL | DIRECT |
|---|---|---|---|
| Test/blank/standard | 10 | | 10 |
| HCI | 25 | | 50 |
| Caffeine | 50 | | 0 |
| Diazo | 0 | | 25 |
| Cysteine | 5 | | 5 |
| Alkaline tartrate | 75 | | 75 |

The plate should be read within 1 minute of adding the alkaline tartrate for maximum absorbance and reproducibility. Read the plate at 600 nm.

Calculation

The concentration of bilirubin in the sample can be calculated from the standard curve. The total volume in each well is 165 µL.

Parameters of the Assay

The lowest bilirubin concentration that can be reliably and reproducibly assayed using this procedure is 0.1 mg/dL. The concentration-absorbance relation remains linear to 40 mg/dL, beyond this, samples should be diluted appropriately.

Through experimentation, hemoglobin concentrations up to 300 mg/dL do not affect the accuracy of this assay. Hemoglobin concentrations beyond this up to around 600 mg/dL may be reduced to within the acceptable range by treatment with an equal volume of saturated EDTA solution followed by 2 minutes of centrifugation at 13,000 rpm to remove precipitated iron-containing moieties.

EXAMPLE 8

This example illustrates a model of sentinel (low volume) SAH which may be used to measure CSF bilirubin as a means for identification of an SAH and exclusion of the diagnosis of traumatic spinal tap. The measurement of CSF bilirubin, if collected 12 hours after the onset of symptoms, can distinguish between a SAH and a traumatic spinal tap. Furthermore, the bilirubin production occurs over a predictable time-course that can be detected after a low-volume SAH. It is believed that hemorrhage, hemolysis, and hemoglobin degradation after an SAH lead to the production of bilirubin whereas a traumatic LP contains relatively little bilirubin. The timing and processes involved in the production of bilirubin in CSF following sentinel aSAH are demonstrated.

Bilirubin Assay.

Total bilirubin was assayed using a method based on those developed by Michaelsson and Nosslin and adapted for use in a microtiter plate by the inventors (GJPG and JFC). Briefly, samples was treated with a caffeine/benzoic acid reagent in order to make all the bilirubin available for the diazotization reaction. A Diazo reagent was added to yield the pink azobilirubin compound, and this moiety was then stabilized with a cysteine reagent and alkalinized with alkaline tartrate reagent to yield a blue coloration. This color change minimizes hemoglobin interference.

In vivo Experiments

Two-month-old male Yorkshire pigs weighing 16-20 kg were utilized for the porcine model of an SAH. All animals were initially anesthetized with intramuscularly delivered ketamine (30 mg/kg) followed by intravenously administrated pentobarbital (35 mg/kg) through an ear vein to obtain deep surgical levels of anesthesia. After pentobarbital anesthesia induction, pigs were intubated with a cuffed endotracheal tube per os and mechanically ventilated using a mechanical respirator (supplemented with 1 L/minute oxygen). In one animal, endotracheal intubation was unsuccessful and a tracheostomy was performed. Using a cut-down in the right groin, the femoral artery and vein were exposed, and the femoral artery was catheterized. This arterial catheter provided a recording of blood pressure and heart rate and was used for obtaining blood samples (0.5 mL) for respiratory blood gas analysis, acid-base status, and hematocrit. Blood samples withdrawn during the control period and following SAH induction were analyzed for $pO_2$, $pCO_2$, pH and base deficit using a Corning model #168 acid-base and respiratory gas analyzer. Pentobarbital was infused continuously via a femoral vein catheter at a rate of approximately 20 mg/kg/hr throughout the remainder of the experiment to maintain a constant level of anesthesia. The depth of anesthesia was tested by the absence of limb withdrawal response to painful pinch, as well as, by monitoring increases in arterial blood pressure and heart rate. Body temperature, measured using a rectal thermistor probe, was maintained at 38.0±0.5° C. with a warm water blanket and portable thermal fan. In order to access the lumbar cistern, a dorsal midline incision exposed the spinous processes of the lower lumbar spine and the upper sacrum. The paraspinous musculature was reflected laterally using sub-periosteal dissection. Hemostasis was achieved with monopolar cautery. A 22 gauge spinal needle was inserted into the interlaminar space (either L4/5 or L5/S1) to penetrate the ligamentum flavum and then the dura mater. The purpose of the surgical exposure prior to the spinal tap was to facilitate a traumatic spinal tap. Spinal fluid was then collected, centrifuged, and labeled as time zero. The spinal needle's stylet was reinserted, and the needle was left in place for the remainder of the experiment. CSF volumes of 0.1 mL were then collected from the lumbar cistern in 1-2 hr intervals for a total of 24 hours post-injection of blood or saline (see below). Immediately upon collection, CSF was immediately centrifuged and stored at −30° C. until analysis.

The animals' cisterna magnae were accessed using a midline incision at the craniocervical junction. The muscles of the posterior neck were reflected laterally, and the rectus capitus minimus was identified between the opisthion of the occiput to the upper boarder of the atlas. Mobilization of the rectus capitus minimus exposed the atlanto-occipital membrane. An 18 gauge spinal needle was then inserted through the atlanto-occipital membrane and the dura mater to reach the cisterna magna. A small amount of CSF egressing from the needle confirmed correct location. The initial CSF was collected, centrifuged, labeled as time zero, and stored (−30° C.). Injections of either 250 µL whole arterial non-heparinized blood or 250 µL of 0.9% sodium chloride were administered via the spinal needle. The spinal needle's stylet was reinserted, and the needle was left in place for the remainder of the experiment. Cisternal CSF samples (100 µL) were serially collected in 1-2 hr intervals thereafter, and immediately upon collection, the CSF was centrifuged and stored for assay (−30° C.).

Four animals were in the experimental arm, each with a 250 µL volume of blood delivered to their cisterna magna. Three control animals were completed, each with the injection of 250 µL of isotonic (0.9%) saline into their cisterna magna.

Statistical Methods.

First, a regression curve was fitted to the bilirubin data as a function of time. This was done separately for CM and LP data. The 95% prediction limits were obtained around the fitted curve, and the upper 95% confidence limit of the control group mean was compared with the lower 95% predicted limits for the curve. An AP value of $\leq 0.05$ was considered statistically different. The earliest time point where the two limits separated from each other (i.e., did not overlap) was declared to be the time (in hours) since the "beginning" of the experiment, when the CSF bilirubin significantly exceeded control group values. This analysis was also confirmed by Standard ANOVA procedure, where the control group least square (LS) means were compared with the SAH bilirubin LS means.

Results

In vivo Experiments.

In this porcine model of aSAH, sequential analysis demonstrated consistent and reproducible bilirubin elevations in lumbar cistern and cisterna magna CSF bilirubin concentrations sampled from the aSAH animals. Conversely, concentrations of CSF bilirubin in the control animals did not rise significantly above baseline values. FIG. 1 shows the time course of bilirubin production in our model. There is a significant elevation at 12 hours in both CM and LP CSF from the SAH group, but not the control group. Mean concentrations of bilirubin (±SD) obtained from the lumbar cistern 24 hours following the injection of saline or blood were 4.38±1.04 µM in the SAH animals (n=4) and 1.02±0.05 µM in the control animals (n=3). At 24 hours post-injection, cisterna magna bilirubin concentrations (±SD) were 7.29±1.33 µM and 1.33±0.14 µM in the SAH animals (n=4) and in the control animals (n=3), respectively.

The earliest time point where the control and SAH CSF bilirubin values did not overlap was determined. This analysis was analyzed by Standard ANOVA procedure where means were compared between the control group's least square and the SAH bilirubin. Lumbar puncture & cisterna magna data means significantly differed at 12 hours and that 12-hour point was the first significant difference between the groups (p=0.05 for LP, and p=0.007 for CM).

Table 4 shows the bilirubin concentration found in the pig's serum. Also shown is the average of the zero time point (control CSF) [Br] and the bilirubin concentration found in CSF taken via a deliberately traumatic tap after the 24 hour time point in the control animals.

Bilirubin Production

This experiment evidences that bilirubin production occurs in the porcine subarachnoid space after a sentinel a SAH. Additionally, there was a lack of bilirubin production following sham injection. The production of bilirubin followed a reproducible time course caused by known degradation processes of blood-derived heme. Following a lag period during which HO-1 is induced, the substrate heme is eventually metabolized to bilirubin. If differential CSF bilirubin analysis is extended to clinical application, the observed 12 hour time lag is complimentary to the ultrasensitive phase of computed tomography, which is up to 12 hours. In fact, the time-course of bilirubin production is precisely the value of this diagnostic modality. It is also important to note that there is no significant production of bilirubin in the hemorrhagic CSF following a traumatic spinal tap model (see Table 4). Thus, blood introduced during a traumatic tap will not have sufficient time for the catabolic conversion to bilirubin.

Figure 14:
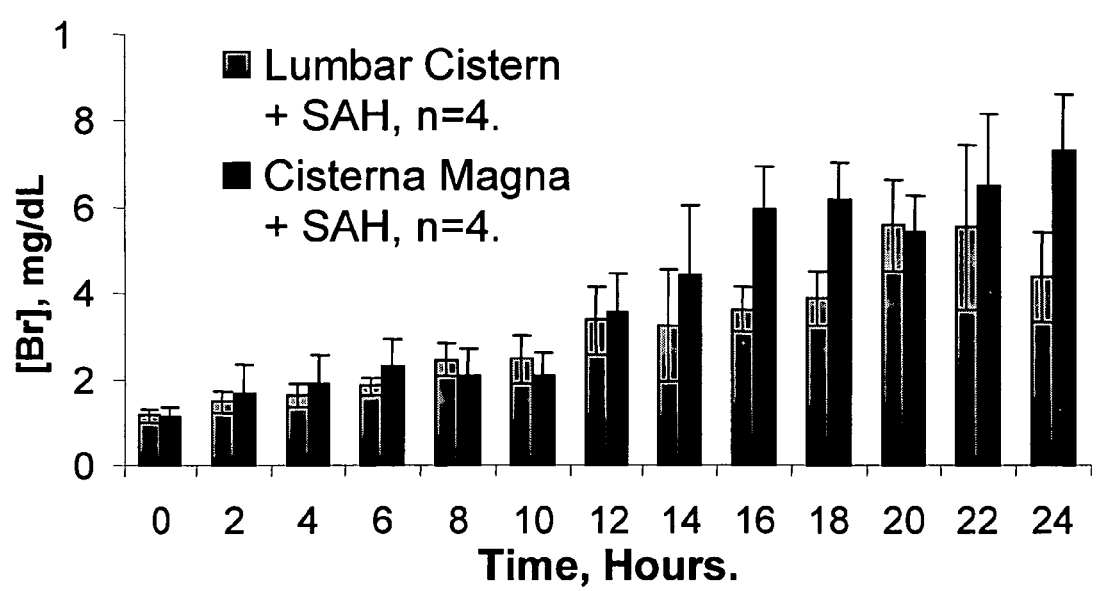
FIG. 14: The production of bilirubin over time in a porcine model of sentinel SAH.

FIG. 14 shows the production of bilirubin over time in a pig model of sentinel SAH. CSF is sampled from the cisterna magna, and via a lumbar puncture, then assayed for bilirubin. The bilirubin concentration becomes statistically significantly greater from saline control values at 12 hours in the cisternal and lumbar samples. Control values for both groups averaged 0.99±0.28 (maximum 1.38, minimum 0.4) mg/dL. Errors are sd.

TABLE 4

| Tissue | [Br], MG/DL | sd | N |
|---|---|---|---|
| Serum | 4.15 | 0.50 | 7 |
| CSF (t0) | 1.22 | 0.23 | 7 |
| Traumatic tap CSF | 1.20 | 0.20 | 3 |

EXAMPLE 9

This example illustrates how the statistical analysis algorithm is employed to estimate the concentration of bilirubin in CSF. The algorithm determines the concentrations of Br and Hb in unknown CSF solution. Spectral analysis provides the absorbance curves for mock CSF for various combinations of Br and Hb respectively. The collected curves are cleaned using box car averaging technique that performs low pass filtering. This step assists in eliminating high frequency noise components from the curves. The premise of this algorithm is generating a relationship between the shape of the absorbance curve, and the concentrations of Br and Hb respectively. Therefore, for example, if the shape of the curve and the Hb concentration is known, the Br concentration may be determined using this relationship.

To accomplish this, the wavelength range where both components contribute significantly to the shape of the mock CSF absorption spectrum is ascertained. The range of 450-500 nm fits this criterion. The system is modeled using multiple linear regression analysis to map the outputs (Br concentration) to known values of mock CSF absorption curves and Hb concentration. Therefore, to determine the Br value the above model requires an estimated Hb concentration along with the absorbance data. The wavelength range of 500-600 nm is chosen where Hb dominates. The bilirubin absorbance is constrained to a low value that remains approximately constant. Linear regression analysis is used again to determine the relationship between the Hb concentration and mean absorbance in this range. For an unknown sample of CSF, the latter range is used to estimate the Hb concentration. The combination of this predicted value and the unknown absorbance data serves as an input to the multiple regression model that outputs the Br concentration.

A Step by Step Description of the Algorithm Flow
Step 1—Sample Analysis
The first step is creating a data set from known concentrations of bilirubin, methemoglobin and mock CSF (manually mixing the bilirubin and methemoglobin). By chemically assaying the samples, obtain the actual concentration of the tested samples is obtained. Eight different concentrations of bilirubin, methemoglobin and the mock solutions are prepared. In addition, 12 different measurements of each sample concentration are analyzed to predict the instrument and human error so that it may be incorporated in the algorithm.

Step 2—Spectral Analysis
The second step of the algorithm this range is used to estimate the Br concentration. Using the spectrometer and its data acquisition software, we collect the data for varying concentrations of
bilirubin (Br), methemoglobin (Hb) and mock CSF (CSF)
This is an essential step of the algorithm. The wavelength ranges are chosen such that the absorbance curve is completely represented. In earlier sections, it is mentioned that a hump occurs in the range of 450-500 nm if excess (>1 mg/dL) bilirubin is present in a mock CSF curve. Therefore, the two wavelength ranges for the entire mock CSF spectrum are chosen. The first range is where only one of the two components, in this case, methemoglobin, is making a significant contribution to the absorption curve, and the second is where the bilirubin and methemoglobin components both actively contribute to the curve. The first range is found to be about 500-600 nm. Spectral analysis of all the samples across concentrations yields an average value of Br absorption from 0.04 to 0.05 across this wavelength range. This is less than the average Hb absorption for the same range by a factor of 10 when the Hb concentrations vary. In the second range of 450 to 500 rn, both of the components [Br and Hb] in mock CSF are active. The absorption spectrum for this wavelength range contains information indicating a fall in Hb absorption and a rise in Br absorption. Therefore, the shape of the mock CSF absorption curve in this range is a function of both Br and Hb concentrations.

Step 3—Training the Hb; Generating the Linear Regression Model from Hb Concentrations
This algorithmic step is used to estimate the Hb concentration by considering the contribution of Br to the mock CSF absorption spectrum as a bias of 0.045 in the defined range. Next, a least squares linear fit is obtained between the estimated concentration of Hb and the mean value of mock CSF absorption from 500-600 nm range. This yields the linear regression model for estimating Hb concentrations in a sample of unknown concentration. The estimated Hb concentration is subsequently used in the mock CSF regression model, developed using the second wavelength range from 450 to 500 nm, and the Br concentration is the output.

Figure 15:
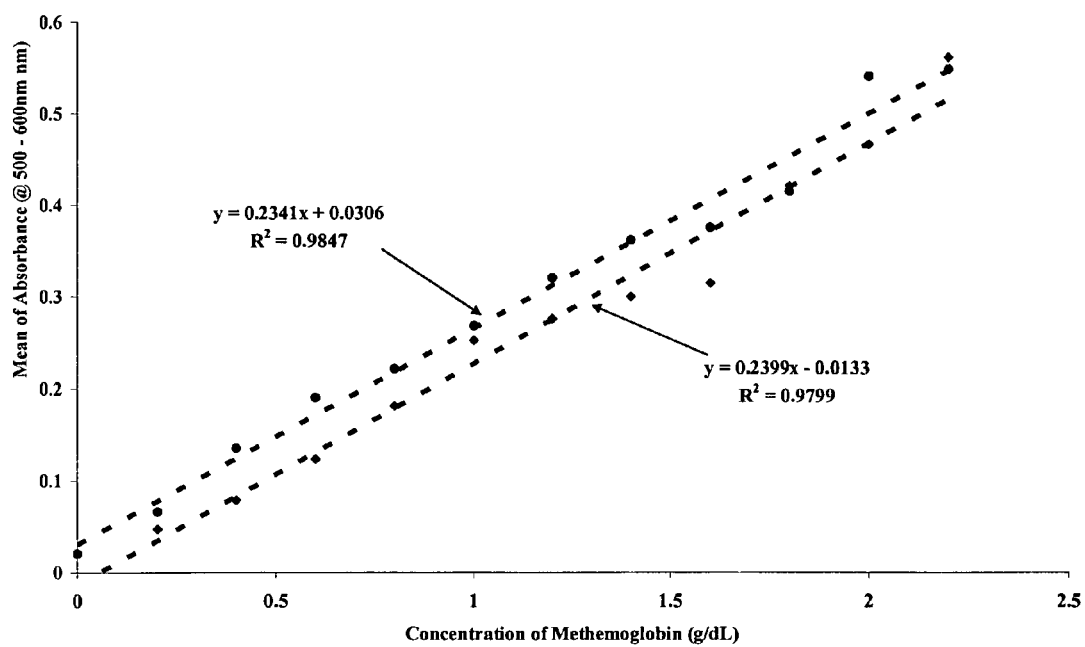
FIG. 15: The approximated linear regression for Hb* condition. It is seen after analyzing the samples instead of fitting the regression models to one particular line, two lines (max and min) and evaluated.

The approximated linear regression for Hb across the 500-600 nm wavelength range is shown in FIG. 15. Rather than fitting the regression models to one particular line, two lines (max and min) are evaluated. The confidence ($R^2$) is high (0.97-0.98) showing the high degree of correlation. The ($R^2$) value was for design and was always 0.95 or above to obtain better accuracy and less error in the overall algorithm.

Step 4—Training the Br
From 450 to 500 nm both the components in mock CSF are active. The absorption spectrum for the wavelengths here contains information indicating uneven relative absorption between Hb and Br. There are wavelengths wherein Hb absorption is greater than Br, Hb is less than Br, and points where their absorptions are approximately equal. Hence it can be said that the shape of the mock CSF absorption curve in this range is a function of both Br as well as Hb concentrations. This forms the basis of fitting the regression model. The estimated Hb concentration may be used to resolve Step 5—Obtaining the Br Concentration Steps 3 and 4 provide the regression models for Hb and Br respectively. The output in this case is the Br concentration [Estimated Br].

Input the mock CSF absorbance spectra into the Hb regression model

Output is an estimated Hb value

Input the estimated Hb and mock CSF absorbance value into the Br regression model Output is the estimated value of bilirubin

EXAMPLE 10

Figure 16:
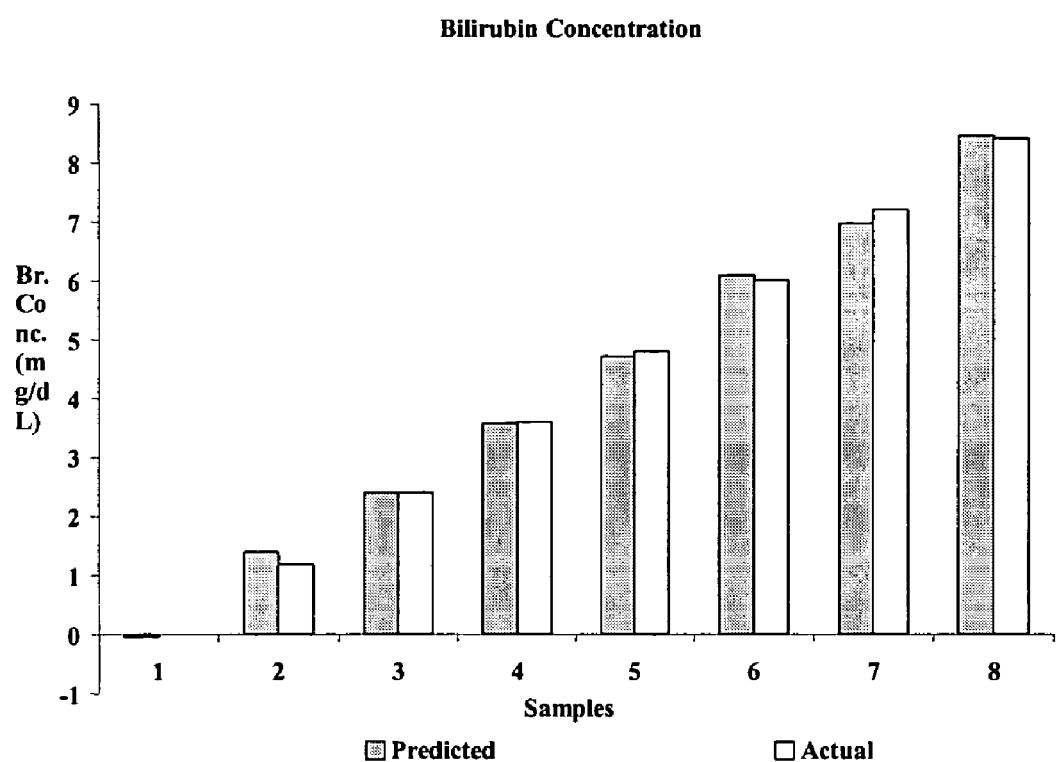
FIG. 16: Estimation of the bilirubin concentration from the linear regression model.
Figure 17:
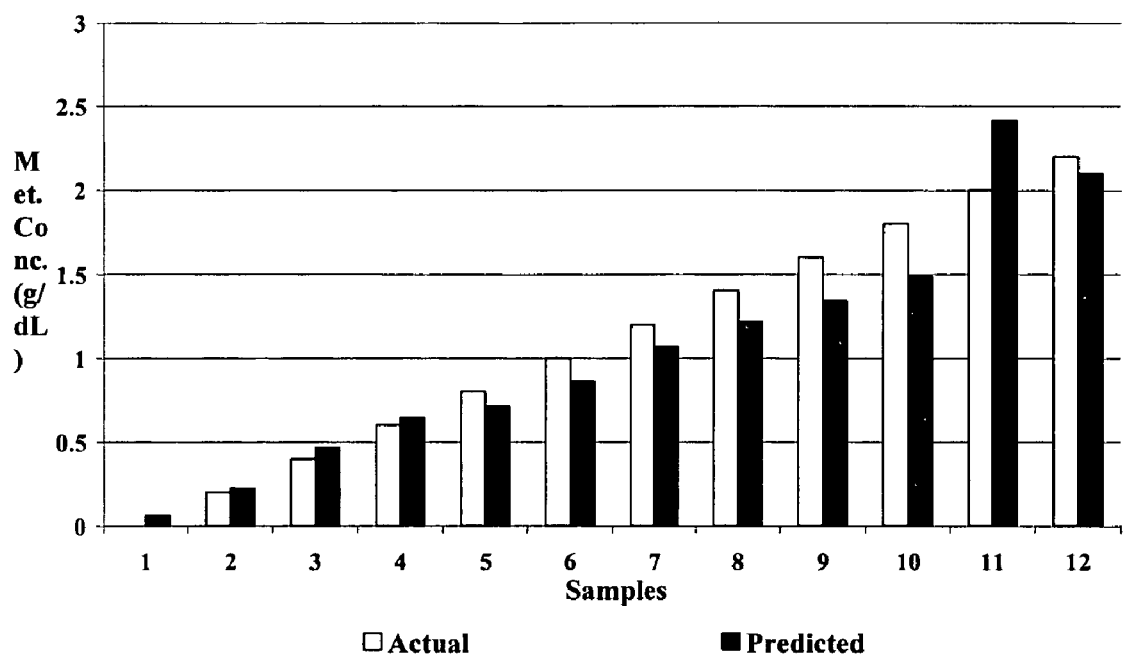
FIG. 17: Estimation of the methemoglobin concentration from the linear regression model.
Figure 18A:
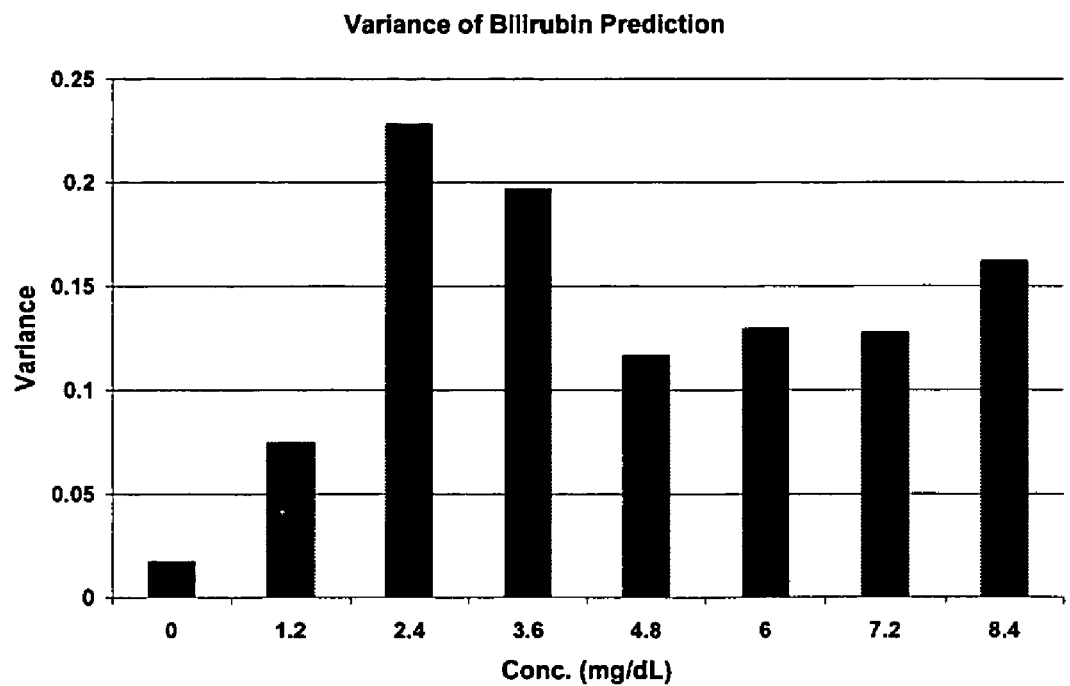
FIG. 18a: The variance of prediction for Bilirubin for noise.

This example reports the results of estimating concentrations of bilirubin in sample mock CSF using the bio-statistical approach for the following cases:

Case 1:
  Predict Methemoglobin—zero noise condition
  Predict Br—zero noise condition
  Variance of prediction for Br—zero noise Case 2:
  Prediction of Br—random noise component introduced
  Variance of prediction for Br—random noise component introduced Case 1: Predict Methemoglobin/Prediction of Br—Zero Noise Condition The prediction of hemoglobin is achieved when a mock CSF solution is run on the Hb model. The regression model shown in FIG. 15 is used for determining the estimated value of Hb. As FIG. 17 shows the estimated value of Hb shows good fit to the actual values. Currently, the model is being improved to accommodate more samples and improve the regression model for Hb. Our primary objective in this paper is to determine the predicted bilirubin values. As shown in FIG. 16, the predicted and the actual (Gold Standard—obtained by assay) are plotted for noise free data. It is observed that the values at varying concentrations predict efficiently. In terms of statistics the variance of the prediction is shown in FIG. 18a. This defines how spread out the predicted value is from the actual value (within 95% of the mean distribution value).

Case 2: Predicted Bilirubin/Variance of Prediction—Noisy Condition

The same analysis is repeated with a random noise data. There are two primary reasons to incorporate this type of analysis:
  To determine the robustness of the model
  To incorporate the error factor that is generated during data collection (STEP 1)
    a. Human error—caused when collecting data (preparation of the solution)
    b. Instrumental error—caused by spectrometer itself.

Figure 18B:
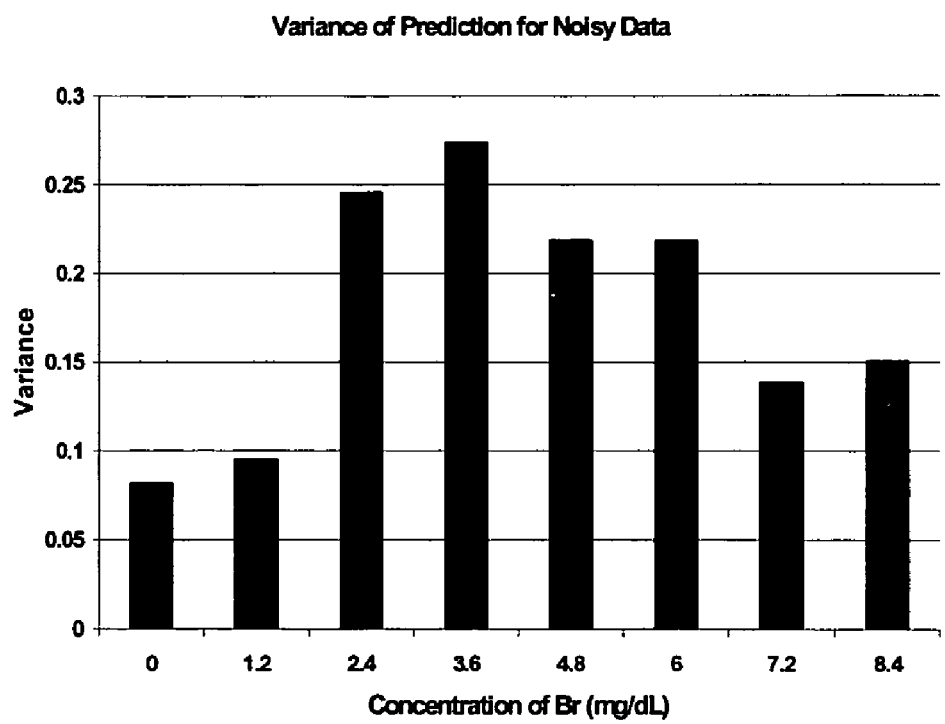
FIG. 18: The variance of prediction for Bilirubin for zero noise.
Figure 19:
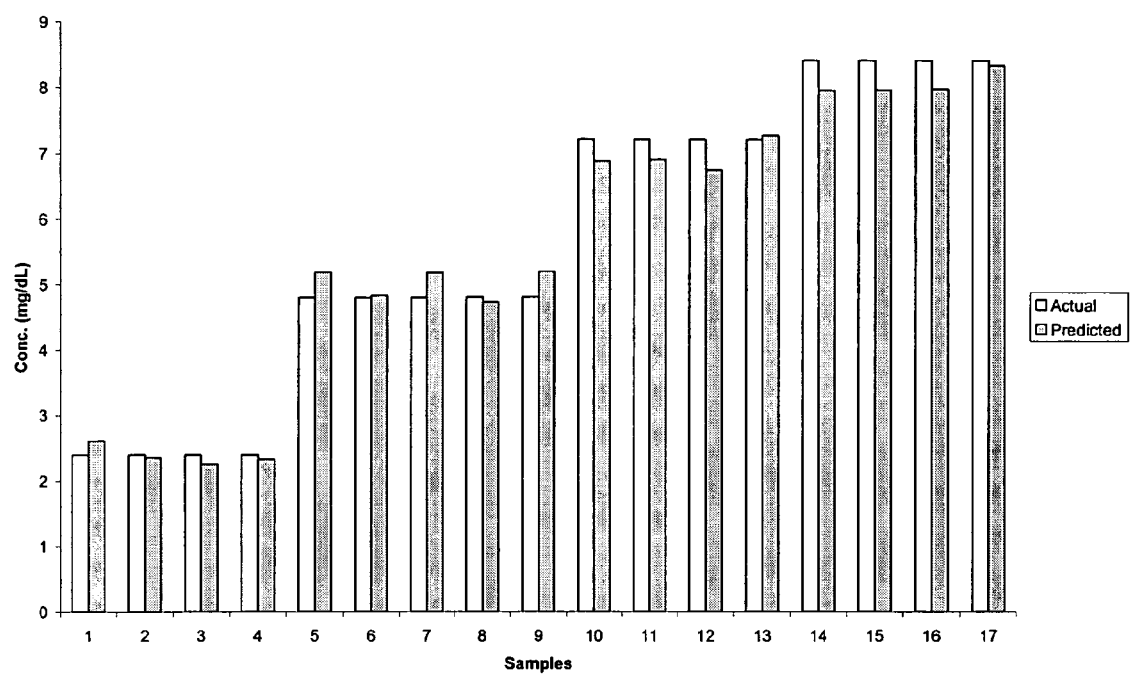
FIG. 19: Bilirubin prediction in random noise.

The variance of prediction is shown in FIG. 18b, and Br prediction indicates that the algorithm is also acceptably robust for noisy environment.

What is claimed is:

1. A point-of-care method for assessing whether a condition in an individual is a hemorrhagic condition, comprising the steps of:
  (a) obtaining a cerebrospinal fluid sample comprising at least one analyte from an individual;
  (b) analyzing the cerebrospinal fluid sample by a spectrophotometer which scans an entire spectral wavelength range of from about 350 nm to about 650 nm and determines absorption data of at least one analyte in the sample over the entire spectral wavelength range;
  (c) determining a concentration of at least one analyte in the sample by applying a mathematical algorithm to the absorption data over the entire spectral wavelength range of step (b); and
  (d) assessing at the point-of-care of the individual whether the condition of the individual is a hemorrhagic condition based on the concentration of at least one analyte determined in step (c),
  wherein the concentration of at least one analyte in the sample may be determined in the presence of one or more additional proteins in the sample.

2. The method according to claim 1, wherein the spectral wavelength range is from about 450 to about 500 nm or from about 390 to about 420 nm, or both.

3. The method according to claim 1, wherein the spectral wavelength range is from about 486 nm to about 524 nm.

4. The method according to claim 1, further comprising the step of constructing a spectral absorption curve from the absorption data, wherein the spectral absorption curve plots absorption versus wavelength.

5. The method according to claim 1, wherein the at least one analyte comprises methemoglobin, oxyhemoglobin, deoxyhemoglobin, bilirubin, or a combination thereof.

6. The method according to claim 4, further comprising the step of determining the concentration of methemoglobin, oxyhemoglobin, deoxyhemoglobin, bilirubin or a combination thereof from a mathematical algorithm applied to the spectral absorption curve.

7. The method according to claim 6, wherein the mathematical algorithm comprises a linear regression algorithm, a modified minimum distance algorithm, a first or second order derivative algorithm, or some combination thereof.

8. The method according to claim 1, wherein the analysis of the cerebrospinal fluid sample comprises determining a length of time since blood was introduced into the cerebrospinal fluid.

9. The method according to claim 8, wherein the length of time since blood was introduced into the cerebrospinal fluid correlates with the concentration of at least one analyte in the cerebrospinal fluid sample.

10. The method according to claim 8, wherein the length of time-since blood was introduced into the cerebrospinal fluid is used to assess a course of therapy for the condition.

11. The method according to claim 8, wherein the length of time since blood was introduced into the cerebrospinal fluid is used to design a therapy for the condition.

12. The method according to claim 1, wherein the analysis of the cerebrospinal fluid sample comprises determining an amount of blood in the cerebrospinal fluid sample.

13. The method according to claim 12, wherein the amount of blood in the cerebrospinal fluid sample correlates to a level of severity of the condition.

14. The method according to claim 1, wherein the hemorrhagic condition is selected from the group consisting of stroke, head injury, hemorrhage subarachnoid hemorrhage, arterial malformation, venous malformations, tumor, or a combination thereof.

15. The method according to claim 1, wherein the condition comprises a hemorrhage.

16. The method according to claim 1, wherein the individual is suspected of having suffered a subarachnoid hemorrhage.

17. The method according to claim 1, further comprising the step of obtaining sequential cerebrospinal fluid samples from the individual.

18. The method according to claim 17, wherein the sequential samples are analyzed to assess a level of severity of the condition.

19. The method according to claim 17, wherein the sequential samples are analyzed to assess efficacy of a treatment.

20. The method according to claim 15, further comprising the step of obtaining sequential cerebrospinal fluid samples from the individual.

21. The method according to claim 20, further comprising the step of analyzing the sequential samples to determine if the hemorrhage is continuing or resolving.

22. The method according to claim 8, wherein the condition comprises a hemorrhage.

23. The method according to claim 22, wherein the length of time since blood was introduced into the cerebrospinal fluid is used to confirm a time the hemorrhage occurred.

24. The method of claim 1, further comprising the step of assessing whether the presence of the analyte in the cerebrospinal fluid sample is the result of traumatic spinal tap, based on the concentration of at least one analyte determined in step (c).

25. A point-of-care method for diagnosing a subarachnoid hemorrhage, the method comprising the steps of:
   (a) obtaining a cerebrospinal fluid sample comprising at least one analyte from an individual suspected of having a subarachnoid hemorrhage;
   (b) analyzing the cerebrospinal fluid sample by a spectrophotometer which scans an entire spectral wavelength range of from about 350 nm to about 650 nm and determines absorption data of at least one analyte in the sample over the entire spectral wavelength range;
   (c) determining a concentration of at least one analyte in the sample by applying a mathematical algorithm to the absorption data over the entire spectral wavelength range of step (b); and
   (d) determining at the point-of-care of the individual whether the individual is suffering from a subarachnoid hemorrhage based on the concentration of at least one analyte determined in step (c), wherein the concentration of at least one analyte may be determined in the presence of one or more additional proteins in the sample.

26. The method of claim 25, wherein the at least one analyte is selected from the group consisting of bilirubin, oxyhemoglobin, methemoglobin, deoxyhemoglobin, and combinations thereof.

\* \* \* \* \*